(12) United States Patent
Mazurov et al.

(10) Patent No.: US 8,859,609 B2
(45) Date of Patent: Oct. 14, 2014

(54) NICOTINIC ACETYLCHOLINE RECEPTOR SUB-TYPE SELECTIVE AMIDES OF DIAZABICYCLOALKANES

(75) Inventors: Anatoly Mazurov, Greensboro, NC (US); Lan Miao, Advance, NC (US); Yunde Xiao, Clemmons, NC (US)

(73) Assignee: Targacept, Inc., Winston-Salem, NC (US)

( * ) Notice: Subject to any disclaimer, the term of this patent is extended or adjusted under 35 U.S.C. 154(b) by 379 days.

(21) Appl. No.: 13/342,635

(22) Filed: Jan. 3, 2012

(65) Prior Publication Data
US 2013/0005789 A1  Jan. 3, 2013

Related U.S. Application Data

(62) Division of application No. 12/447,850, filed as application No. PCT/US2007/083330 on Nov. 1, 2007, now Pat. No. 8,114,889.

(60) Provisional application No. 60/856,079, filed on Nov. 2, 2006.

(51) Int. Cl.
    *A61K 31/40*     (2006.01)
    *C07D 471/08*    (2006.01)
    *C07D 487/04*    (2006.01)

(52) U.S. Cl.
    CPC ............ *C07D 471/08* (2013.01); *C07D 487/04* (2013.01)
    USPC ........................................................ 514/414

(58) Field of Classification Search
    None
    See application file for complete search history.

(56) References Cited

U.S. PATENT DOCUMENTS

| | | |
|---|---|---|
| 4,922,901 A | 5/1990 | Brooks et al. |
| 5,468,858 A | 11/1995 | Berlin et al. |
| 5,583,140 A | 12/1996 | Bencherif et al. |
| 5,597,919 A | 1/1997 | Dull et al. |
| 5,604,231 A | 2/1997 | Smith et al. |
| 5,616,716 A | 4/1997 | Dull et al. |
| 5,663,356 A | 9/1997 | Ruecroft et al. |
| 5,852,041 A | 12/1998 | Cosford et al. |
| 5,853,696 A | 12/1998 | Elmaleh et al. |
| 5,952,339 A | 9/1999 | Bencherif et al. |
| 5,969,144 A | 10/1999 | London et al. |
| 6,815,438 B2 | 11/2004 | Peters et al. |
| 7,314,870 B2 | 1/2008 | Peters et al. |
| 2004/0186107 A1 | 9/2004 | Schrimpf et al. |
| 2005/0101602 A1 | 5/2005 | Basha et al. |
| 2005/0234031 A1 | 10/2005 | Schrimpf et al. |
| 2006/0019985 A1 | 1/2006 | Ma et al. |

FOREIGN PATENT DOCUMENTS

| | | |
|---|---|---|
| WO | WO 94/08992 | 4/1994 |
| WO | WO 96/07656 | 3/1996 |
| WO | WO 96/31475 | 10/1996 |
| WO | WO 96/40682 | 12/1996 |
| WO | WO 02/070523 A1 | 9/2002 |
| WO | WO 2004/016616 A1 | 2/2004 |
| WO | WO 2004/076453 A1 | 9/2004 |
| WO | WO 2006/124748 A2 | 11/2006 |

OTHER PUBLICATIONS

Mazurov et al (J Med Chem 55:9181-9194, 2012).*
Papke et al (Brit J Pharmacol 120:429-438, 1997).*
Int'l Search Report, Apr. 18, 2008.
Arneric, S., of al., "Cholinergic channel modulators as a novel therapeutic strategy for Alzheimer's disease," *Exp. Opin. Invest. Drugs*, 5(1): 79-100 (1996).
Arneric, S., et al., "Preclinical Pharmacology of ABT-418: A Prototypical Cholinergic Channel Activator for the Potential Treatment of Alzheimer's Disease," *CNS Drug Rev.*, 1(1): 1-26 (1995).
Bannon, A.W., et al., "Broad-Spectrum, Non-Opioid Analgesic Activity by Selective Modulation of Neuronal Nicotinic Acetylcholine Receptors," *Science*, 279: 77-80 (1998).
Bencherif M. and R.J. Lukas, "Differential Regulation of Nicotinic Acetylcholine Receptor Expression by Human TE671/RD Cells Following Second Messenger Modulation and Sodium Butyrate Treatments," *Mol Cell Neurosc.*, 2(1): 52-65 (1991).
Bencherif, M., and J. D. Schmitt, "Targeting Neuronal Nicotinic Receptors: a Path to New Therapies," *Current Drug Targets 1*(4): 349-357 (2002).
Bencherif, M., and R.J. Lukas, "Ligand Binding and Functional Characterization of Muscarinic Acetylcholine Receptors on the TE671/RD Human Cell Line," *J Pharmacol. Exp. Ther.* 257(3): 946-953 (1991).

(Continued)

*Primary Examiner* — Craig Ricci
(74) *Attorney, Agent, or Firm* — Womble Carlyle Sandridge & Rice, LLP; Amy H. Fix

(57) ABSTRACT

Compounds, pharmaceutical compositions including the compounds, and methods of preparation and use thereof are disclosed. The compounds are amide compounds which can be prepared from certain heteroaryl carboxylic acids and certain diazabicycloalkanes. The compounds exhibit selectivity for, and bind with high affinity to, neuronal nicotinic receptors of the α4β2 subtype in the central nervous system (CNS). The compounds and compositions can be used to treat and/or prevent a wide variety of conditions or disorders, particularly CNS disorders. The compounds can: (i) alter the number of nicotinic cholinergic receptors of the brain of the patient, (ii) exhibit neuroprotective effects, and (iii) when employed in effective amounts, not result in appreciable adverse side effects (e.g. side effects such as significant increases in blood pressure and heart rate, significant negative effects upon the gastrointestinal tract, and significant effects upon skeletal muscle).

2 Claims, 1 Drawing Sheet

(56) References Cited

OTHER PUBLICATIONS

Bencherif, M., et al., "RJR-2403: A Nicotinic Agonist with CNS Selectivity I: In Vitro Characterization," *J. Pharmacol. Exper. Therapeutics*, 279(3): 1413-1421 (1996).
Breining, S.R. et al., "Neuronal Nicotinic Acetylcholine Receptor Modulators: Recent Advances and Therapeutic Potential," *Annual Reports in Medicinal Chemistry*, vol. 40: 3-16 (2005).
Cheng, Yung-Chi, and W.H. Prusoff, "Relationship Between the Inhibition Constant ($K_1$) and the Concentration of Inhibitor which Causes 50 Per Cent inhibition (I50) of an Enzymatic Reaction," *Biochem. Pharmacol.* 22(23): 3099-3108 (1973).
Chiari, A., et al., "Sex Differences in Cholinergic Analgesia I: A Supplemental Nicotinic Mechanism in Normal Females," *Anesthesiology*, 91(5): 1447-1454 (1999).
Coe, J.W. et al., "3,5-Bicyclic aryl piperidines: A novel class of a4132 neuronal nicotinic receptor partial agonists for smoking cessation," Bioorganic & Medicinal Chemistry Letters, 15: 4889-4897 (2005).
Damaj, M.I., et al. « Enantioselective Effects of Hydroxy Metabolites of Bupropion on Behavior and on Function of Monoamine Transporters and Nicotinic Receptors,» Molecular Pharmacology, 66(3) 675-682 (2004).
Damaj, M.I., et al., "Antinociceptive and Pharmacological Effects of Metanicotine, a Selective Nicotinic Agonist,"I Pharmacol. Exp. Ther., 291(1): 390-398 (1999).
Dani, J.A. et al. « Potential applications of nicotinic ligands in the laboratory and clinic, » Bioorganic & Medicinal Chemistry Letters 14 : 1837-1839.
Davies, Andrew R.L., et al., "Characterisation of the binding of [3H]methyllycaconitine: a new radioligand for labeling a7-type neuronal nicotinic acetylcholine receptors," Neuropharmacol. 38: 679-690 (1999).
Decker, M.W., "Nicotinic Acetylcholine Receptor Agonists: A Potential New Class of Analgesics," *Current Topics in Medicinal Chemistry*, 4: 369-384 (2004).
Dwoskin, L.P. and Crooks, P.A., "A novel mechanism of action and potential use for lobeline as a treatment for psychostimulant abuse," *Biochemical Pharmacology*, 63: 89-98 (2002).
Ennaceur, A. and J Delacour, "A New One-Trial Test for Neurobiological Studies of Memory in Rats. 1: Behavioral Data," Behav. Brain Res., 31 47-59 (1988).
Graham, A.J., et al. "Human Brain Nicotinic Receptors, their Distribution and Participation in Neuropsychiatric Disorders," *Current Drug Targets—CNS & Neurological Disorders*, 1: 387-397 (2002).
Greene, T.W. and P.G. M. Wuts, "Protective Groups in Organic Synthesis," 3rd ed. (1999).
Hogg, R.C. and Bertrand, D., "Nicotinic Acetylcholine Receptors as Drugs," Current Drug Targets—CNS & Neurological Disorders, 3: 123-130 (2004).
Holladay, M.W., et al., "Neuronal Nicotinic Acetylcholine Receptors as Targets for Drug Discovery," J Med. Chem., 40(26): 4169-4194 (1997).
Hoyer, D. and Boddeke, H.W.G.M., "Partial agonists, full agonists, antagonists: dilemmas of definition," TiPS Reviews, 14: 270-275 (1993).
Jain, K.K., "Modulators of nicotinic acetylcholine receptors as analgesics," Current Opinion in Investigational Drugs, 5(1): 76-81 (2004).
Jeyaraman, R. and Avila, S., "Chemistry of 3-Azabicyclo[3.3. 1]nonanes," Chemical Rev. 81: 149-174 (1981).
Jonnala, R.R. and Buccafusco, J.J., "Relationship Between the Increased Cell Surface a7 Nicotinic Receptor Expression and Neuroprotection Induced by Several Nicotinic Receptor Agonists," Journal of Neuroscience Research, 66: 565-572 (2001).
Kiso, Y. and H. Yajima, "Amide Formation, Deprotection, and Disulfide Formation in Peptide Synthesis," Peptides, 39-91 Academic Press, San Diego, CA (1995).
Lavand'homme, P.M., and J.C. Eisenach, "Sex Differences in Cholinergic Analgesia II: Differing Mechanisms in Two Models of Allodynia," Anesthesiology, 91(5): 1455-1461 (1999).

Levin, E.D., and A.H. Rezvani, "Nicotinic Treatment for Cognitive Dysfunction," Current Drug Targets: CNS and Neurological Disorders, 1(4): 423-431 (2002).
Lippiello, P.M., et al., "RJR-2403: A Nicotinic Agonist with CNS Selectivity II. In Vivo Characterization," I P. E. T., 279(3): 1422-1429 (1996).
Lowry, et al., "Protein Measurement with the Folin Phenol Reagent," J. Biol. Chem. 193: 265-275 (1951).
Lukas, R.J., "Pharmacological Distinctions between Functional Nicotinic Acetylcholine Receptors on the PC 12 Rat Pheochromocytoma and the TE671 Human Medulloblastoma," J. Pharmacol. Exp. Ther. 251(1): 175-182 (1989).
Lukas, R.J., and M.J. Cullen, "An Isotopic Rubidium Ion Efflux Assay for the Functional Characterization of Nicotinic Acetylcholine Receptors on Clonal Cell Lines," Anal. Biochem. 175(1): 212-218 (1988).
Lukas, R.J., et al., "Characterization of Nicotinic Acetylcholine Receptors Expressed by Cells of the SH-SY5Y Human Neuroblastoma Clonal Line," Molec Cellular Neurosci 4(1): 1-12 (1993).
Luther, et al., "A Muscle Acetylcholine Receptor is Expressed in the Human Cerebellar Medulloblastoma Cell Line TE671," *I Neurosci.* 9(3): 1082-1096 (1989).
Marrero, M.B. et al., "The Neuroprotective Effect of 2-(3-Pyridyl)-1-azabicyclo[3.2.2]nonane (TC-1698), a Novel a7 Ligand, Is Prevented through Angiotensin II Activation of a Tyrosine Phosphatase," *The Journal of Pharmacology and Experimental Therapeutics*, vol. 309 (1) 16-27 (2003).
McEvoy, J.P. and Allen, T.B., "The Importance of Nicotinic Acetylcholine Receptors in Schizophrenia, Bipolar Disorder and Tourette's Syndrome," *Current Drug Targets—CNS & Neurological Disorders*, 1: 433-442 (2002).
Miao, F.J..P. et al. "Central Terminals of Nociceptors are Targets for Nicotine Suppression of Inflammation," *Neuroscience*, 123: 777-784 (2004).
Newhouse, P.A., et al., "Effects of nicotinic stimulation on cognitive performance," Curr. Opin. Pharmacol. 4:36-46 (2004).
O'Neill, M.J., et al., "The Role of Neuronal Nicotinic Acetylcholine Receptors in Acute and Chronic Neurodegeneration," Current Drug Targets: CNS and Neurological Disorders, 1(4): 399-411 (2002).
Oswald, R.E., et al., "Characterization of nicotinic acetylcholine receptor channels of the TE671 human medulloblastoma clonal line," Neurosci. Lett. 96: 207-212 (1989).
Rapier, et al., "Nicotinic Modulation of [3H]Dopamine Release from Striatal Synaptosomes: Pharmacological Characterisation," I Neurochem. 54(3): 937-45 (1990).
Ripoll, N. et al., "Nicotinic receptors and schizophrenia," Current Medical Research and Opinion, 20(7): 1057-1074 (2004).
Sacco, K.A. et al., "Nicotinic receptor mechanisms and cognition in normal states and neuropsychiatric disorders," Journal of Psychopharmacology, 18(4): 457-474 (2004).
Shytle, R.D. et al., "Neuronal Nicotinic Receptor Inhibition for Treating Mood Disorders: Preliminary Controlled Evidence with Mecamylamine," Depression and Anxiety, 16: 89-92 (2002).
Shytle, R.D., et al., "Nicotinic acetylcholine receptors as targets for antidepressants," Molecular Psychiatry, 7: 525-535 (2002).
Stead, D., et al., "Concise Synthesis of (±)-Cytisine via Lithiation of N-Boc-bispidine," Organic Letters, 7(20): 4459-4462 (2005).
Stratton, et al., "Characterization of the human cell line TE671," *Carcinogenesis* 10(5): 899-905 (1989).
Suto, M.J. & Zacharias, N., "Neuronal nicotinic acetylcholine receptors as drug targets," *Expert Opin. Ther. Targets*, 8(2): 61-64 (2004).
Takada, Y. et al., "Nicotinic Acetylcholine Receptor-Mediated Neuroprotection by Donepezil Against Glutamate Neurotoxicity in Rat Cortical Neurons," The Journal of Pharmacology and Experimental Therapeutics, 306(2) 772-777 (2003).
Villemagne, V.L. et al., "Nicotine and Related Compounds as PET and SPECT Ligands," Neuronal Nicotinic Receptors Pharmacology and Therapeutic Opportunities 235-250 (1998).
Vincler, M., "Neuronal nicotinic receptors as targets for novel analgesics," Expert Opin. Investig. Drugs, 14(10): 1191-1198 (2005).

(56) References Cited

OTHER PUBLICATIONS

Whiting, P.J., et al., "Expression of nicotinic acetylcholine receptor subtypes in brain and retina," Molecular Brain Research, 10: 61-70 (1991).

Whiting, P.J., et al., "Functional acetylcholine receptor in PC12 cells reacts with a monoclonal antibody to brain nicotinic receptors," Nature 327 515-518 (1987).

Williams, M., et al., "Neuronal Nicotinic Acetylcholine Receptors," Drug News Perspec., 7(4): 205-223 (1994).

Young, J.M., "Mecamylamine: New Therapeutic Uses and Toxicity/Risk Profile," Clinical Therapeutics, 23(4): 532-565 (2001).

Anderson, "The Process of Structure-Based Drug Design," Chemistry & Biology, vol. 10, pp. 787-797, Chem and Biol, 2003, pp. 787-797.

Thiel, "Structure-Aided Drug Design's Next Generation," Nature Biotechnology, vol. 22, No. 5, May 2004, pp. 513-519.

English translation of Office Action for corresponding Japanese application 2009-535465 dated Jan. 8, 2013.

\* cited by examiner

NICOTINIC ACETYLCHOLINE RECEPTOR SUB-TYPE SELECTIVE AMIDES OF DIAZABICYCLOALKANES

CROSS REFERENCE TO RELATED APPLICATION

This application is a divisional of U.S. patent application Ser. No. 12/447,850, filed Aug. 18, 2009, which claims priority to PCT Application Number PCT/US2007/083330, with an International Filing Date of Nov. 1, 2007, which claims priority to U.S. Provisional Patent Application Ser. No. 60/856,079, filed Nov. 2, 2006, each of which is herein incorporated by reference in its entirety.

FIELD OF THE INVENTION

The present invention relates to compounds that bind to and modulate the activity of neuronal nicotinic acetylcholine receptors, to processes for preparing these compounds, to pharmaceutical compositions containing these compounds and to methods of using these compounds for treating a wide variety of conditions and disorders, including those associated with dysfunction of the central nervous system (CNS).

BACKGROUND OF THE INVENTION

The therapeutic potential of compounds that target neuronal nicotinic receptors (NNRs), also known as nicotinic acetylcholine receptors (nAChRs), has been the subject of several recent reviews (see Breining et al., *Ann. Rep. Med. Chem.* 40: 3 (2005), Hogg and Bertrand, *Curr. Drug Targets: CNS Neurol. Disord.* 3: 123 (2004), Suto and Zacharias, *Expert Opin. Ther. Targets* 8: 61 (2004), Dani et al., *Bioorg. Med. Chem. Lett.* 14: 1837 (2004), Bencherif and Schmitt, *Curr. Drug Targets: CNS Neurol. Disord.* 1: 349 (2002)). Among the kinds of indications for which NNR ligands have been proposed as therapies are cognitive disorders, including Alzheimer's disease, attention deficit disorder and schizophrenia (Newhouse et al., *Curr. Opin. Pharmacol.* 4: 36 (2004), Levin and Rezvani, *Curr. Drug Targets: CNS Neurol. Disord.* 1: 423 (2002), Graham et al., *Curr. Drug Targets: CNS Neurol. Disord.* 1: 387 (2002), Ripoll et al., *Curr. Med. Res. Opin.* 20(7): 1057 (2004), and McEvoy and Allen, *Curr. Drug Targets: CNS Neurol. Disord.* 1: 433 (2002)); pain and inflammation (Decker et al., *Curr. Top. Med. Chem.* 4(3): 369 (2004), Vincler, *Expert Opin. Invest. Drugs* 14(10): 1191 (2005), Jain, *Curr. Opin. Inv. Drugs* 5: 76 (2004), Miao et al., *Neuroscience* 123: 777 (2004)); depression and anxiety (Shytle et al., *Mol. Psychiatry.* 7: 525 (2002), Damaj et al., *Mol. Pharmacol.* 66: 675 (2004), Shytle et al., *Depress. Anxiety* 16: 89 (2002)); neurodegeneration (O'Neill et al., *Curr. Drug Targets: CNS Neurol. Disord.* 1: 399 (2002), Takata et al., *J. Pharmacol. Exp. Ther.* 306: 772 (2003), Marrero et al., *J. Pharmacol. Exp. Ther.* 309: 16 (2004)); Parkinson's disease (Jonnala and Buccafusco, *J. Neurosci. Res.* 66: 565 (2001)); addiction (Dwoskin and Crooks, *Biochem. Pharmacol.* 63: 89 (2002), Coe et al., *Bioorg. Med. Chem. Lett.* 15(22): 4889 (2005)); obesity (Li et al., *Curr. Top. Med. Chem.* 3: 899 (2003)); and Tourette's syndrome (Sacco et al., *J. Psychopharmacol.* 18(4): 457 (2004), Young et al., *Clin. Ther.* 23(4): 532 (2001)).

A limitation of some nicotinic compounds is that they are associated with various undesirable side effects, for example, by stimulating muscle and ganglionic receptors. It would be desirable to have compounds, compositions and methods for preventing and/or treating various conditions or disorders (e.g., CNS disorders), including alleviating the symptoms of these disorders, where the compounds exhibit nicotinic pharmacology with a beneficial effect (e.g., upon the functioning of the CNS), but without significant associated side effects. It would further be highly desirable to provide compounds, compositions and methods that affect CNS function without significantly affecting those receptor subtypes which have the potential to induce undesirable side effects (e.g., appreciable activity at cardiovascular and skeletal muscle sites). The present invention provides such compounds, compositions and methods.

SUMMARY OF THE INVENTION

The present invention provides certain amide compounds which can be formed from certain heteroaryl carboxylic acids and certain diazabicycloalkanes, particularly 3,7-diazabicyclo[3.3.0]octane and 3,7-diazabicyclo[3.3.1]nonane. These amide compounds bind with high affinity to NNRs of the α4β2 subtype, found in the CNS, and exhibit selectivity for the α4β2 subtype over the α7 NNR subtype, also found in the CNS. The present invention also relates to pharmaceutically acceptable salts prepared from these compounds and the pharmaceutical compositions thereof, which can be used for treating and/or preventing a wide variety of conditions or disorders, and particularly those disorders characterized by dysfunction of nicotinic cholinergic neurotransmission or the degeneration of the nicotinic cholinergic neurons. Also provided are methods for treating and/or preventing disorders, such as CNS disorders, and also for treating certain conditions (e.g., alleviating pain and inflammation), in mammals in need of such treatment. The methods involve administering to a subject a therapeutically effective amount of the compounds (including salts) or pharmaceutical compositions including such compounds. Further provided is a method for treatment of disorders selected from the group consisting of age-associated memory impairment, mild cognitive impairment, pre-senile dementia (early onset Alzheimer's disease), senile dementia (dementia of the Alzheimer's type), Lewy body dementia, vascular dementia, Alzheimer's disease, stroke, AIDS dementia complex, attention deficit disorder, attention deficit hyperactivity disorder, dyslexia, schizophrenia, schizophreniform disorder, and schizoaffective disorder. Even further provided is a method for treatment of disorders selected from the group consisting of the treatment of mild to moderate dementia of the Alzheimer's type, attention deficit disorder, mild cognitive impairment and age associated memory impairment.

The pharmaceutical compositions incorporate a compound of the present invention which, when employed in effective amounts, interacts with relevant nicotinic receptor sites of a subject, and hence acts as a therapeutic agent to treat and prevent a wide variety of conditions and disorders. The pharmaceutical compositions provide therapeutic benefit to individuals suffering from such disorders and exhibiting clinical manifestations of such disorders, in that the compounds within those compositions, when employed in effective amounts, can (i) exhibit nicotinic pharmacology and affect relevant nicotinic receptors sites (e.g., act as a pharmacological agonist to activate nicotinic receptors), and/or (ii) elicit neurotransmitter secretion, and hence prevent and suppress the symptoms associated with those diseases. In addition, the compounds have the potential to (i) increase the number of nicotinic cholinergic receptors of the brain of the patient, (ii) exhibit neuroprotective effects, and/or (iii) when employed in effective amounts, to not cause appreciable adverse side effects (e.g., significant increases in blood pressure and heart rate, significant negative effects upon the gastro-intestinal tract, and significant effects upon skeletal muscle). The pharmaceutical compositions comprising the compounds of the invention, are believed to be safe and effective with regards to prevention and treatment of a wide variety of conditions and disorders.

The foregoing and other aspects of the present invention are explained in detail in the detailed description and examples set forth below.

DETAILED DESCRIPTION

Figure 1:
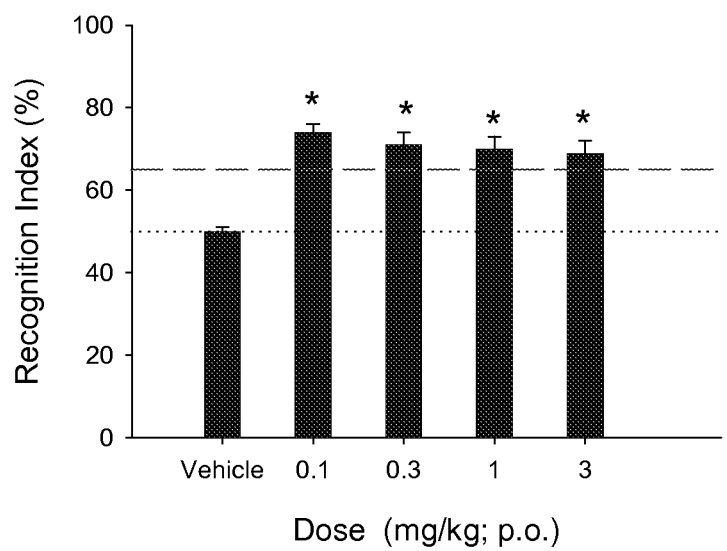
FIG. 1 is a chart showing the results of a study on object recognition in rats treated orally with N-(5-chlorofuran-2-ylcarbonyl)-3,7-diazabicyclo[3.3.0]octane. The results are shown as a function of recognition index (%) versus dose (mg/kg).

The subtype selective compounds, pharmaceutical compositions including these compounds, methods of preparing the compounds, and methods of treatment and/or prevention using the compounds are described in detail below.

The compounds and methods described herein will be better understood with reference to the following preferred embodiments. The following definitions will be useful in defining the scope of the invention:

In this specification, unless stated otherwise, the term "alkyl" includes both straight and branched chain alkyl groups. These may be, but are not limited to, methyl, ethyl, n-propyl, i-propyl, n-butyl, i-butyl, s-butyl, t-butyl, n-pentyl, i-pentyl, neo-pentyl, n-hexyl or i-hexyl. The term "$C_{1-4}$ alkyl" thus includes alkyl groups having 1 to 4 carbon atoms, including, but are not limited to, methyl, ethyl, n-propyl, i-propyl or tert-butyl.

In this specification, unless stated otherwise, the term "cycloalkyl" refers to an optionally substituted, partially or completely saturated monocyclic, bicyclic or bridged hydrocarbon ring system. The term "$C_{3-8}$ cycloalkyl" may be, but is not limited to cyclopropyl, cyclobutyl, cyclopentyl, cyclohexyl, cycloheptyl, and cyclooctyl.

As used herein, heterocyclyl radicals contain from 3 to 10 members including one or more heteroatoms selected from oxygen, sulfur and nitrogen. Examples of suitable heterocyclyl moieties include, but are not limited to, piperidinyl, morpholinyl, pyrrolidinyl, imidazolidinyl, pyrazolidinyl, isothiazolidinyl, thiazolidinyl, isoxazolidinyl, oxazolidinyl, piperazinyl, oxanyl (tetrahydropyranyl), and oxolanyl (tetrahydrofuranyl).

As used herein, $C_{1-6}$ alkoxy radicals contain from 1 to 6 carbon atoms in a straight or branched chain, and also include $C_{3-6}$ cycloalkoxy radicals and alkoxy radicals that contain $C_{3-6}$ cycloalkyl moieties. Examples include, but are not limited to methoxy, ethoxy, propoxy, isopropoxy, butoxy, t-butoxy, isobutoxy, cyclopropylmethoxy, allyloxy or propargyloxy.

As used herein, "aromatic" refers to 3 to 10, preferably 5 and 6-membered ring aromatic and heteroaromatic rings.

As used herein, "aromatic group-containing species" refers to moieties that are or include an aromatic group. Accordingly, phenyl and benzyl moieties are included in this definition, as both are or include an aromatic group, and pyridinyl and pyrimidinyl are included in the definition, as both are heteroaromatic, a subset of aromatic.

As used herein, aryl radicals are selected from phenyl, naphthyl and indenyl.

As used herein, heteroaryl radicals contain from 3 to 10 members, preferably 5 or 6 members, including one or more heteroatoms selected from oxygen, sulfur and nitrogen. Examples of suitable 5-membered ring heteroaryl moieties include furanyl, thienyl, pyrrolyl, imidazolyl, oxazolyl, thiazolyl, isoxazolyl, isothiazolyl, oxadiazolyl, tetrazolyl, triazolyl, and pyrazolyl. Examples of suitable 6-membered heteroaryl moieties include pyridinyl, pyrimidinyl, pyrazinyl, and pyridazinyl. Examples of 9-membered heteroaryl groups include benzimidazolyl, indolizinyl, indolyl, purinyl and indolinyl. Examples of 10-membered heteroaryl groups include quinolinyl and isoquinolinyl.

It will be appreciated that throughout the specification, the number and nature of substituents on rings in the compounds of the invention will be selected so as to avoid sterically undesirable combinations.

Certain compound names of the present invention were generated with the aid of computer software (ACDLabs 8.0/Name(IUPAC)).

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. Nos. 5,597,919 to Dull et al., 5,616,716 to Dull et al. and 5,663,356 to Ruecroft et al.

The compounds of Formula I and pharmaceutically acceptable salts thereof may exist in solvated, for example hydrated, as well as unsolvated forms, and the present invention encompasses all such forms.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., *Trends Pharmacol. Sci.* 14(7): 270-5 (1993). Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As used herein, neurotransmitters whose release is mediated by the compounds described herein include, but are not limited to, acetylcholine, dopamine, norepinephrine, serotonin and glutamate, and the compounds described herein function as modulators at the α4β2 subtype of the CNS NNRs.

Compounds

The compounds described herein are amide compounds formed from certain heteroaryl carboxylic acids and certain diazabicycloalkanes. These compounds can be represented as Formula I:

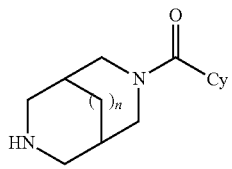

Formula I wherein n has the value of 0 or 1, and Cy is a heteroaryl group chosen from the group of 2-furanyl, 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl and 4-pyridinyl, which heteroaryl groups are optionally substituted with up to three non-hydrogen substituents independently selected from $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-8}$ heterocyclyl, substituted $C_{3-8}$ heterocyclyl, $C_{3-8}$ cycloalkyl, substituted $C_{3-8}$ cycloalkyl, $C_{5-10}$ aryl, $C_{5-10}$ heteroaryl, substituted $C_{5-10}$ aryl, substituted $C_{5-10}$ heteroaryl, $C_{1-6}$ alkyl-$C_{5-10}$ aryl, $C_{1-6}$ alkyl-$C_{5-10}$ heteroaryl, substituted $C_{1-6}$ alkyl-$C_{5-10}$ aryl, substituted $C_{1-6}$ alkyl-$C_{5-10}$ heteroaryl, $C_{5-10}$ aryl-$C_{1-6}$ alkyl, $C_{5-10}$ heteroaryl-$C_{1-6}$ alkyl, substituted $C_{5-10}$ aryl-$C_{1-6}$ alkyl, substituted $C_{5-10}$ heteroaryl-$C_{1-6}$ alkyl, halo, —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", and —NR'SO$_2$R", where R' and R" are independently selected from hydrogen, $C_{1-6}$ alkyl, $C_{3-8}$ cycloalkyl, $C_{3-8}$ heterocyclyl, $C_{5-10}$ aryl, $C_{5-10}$ heteroaryl or $C_{5-10}$ aryl-$C_{1-6}$ alkyl, or R' and R" and the atoms to which they are attached together can form a $C_{3-8}$ heterocyclic ring, wherein the term "substituted", as applied to alkyl, alkenyl, alkynyl, heterocyclyl, cycloalkyl, aryl, heteroaryl, alkylaryl, alkylheteroaryl, arylalkyl and heteroarylalkyl, refers to substitution by one or more alkyl, aryl, heteroaryl, halo, —OR' and —NR'R" groups, or pharmaceutically acceptable salts thereof.

One embodiment of the invention relates to compounds of Formula I wherein n has the value of 0 or 1, and Cy is a $C_{5-10}$ heteroaryl group chosen from the group of 2-furanyl or 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl and 4-pyridinyl, which heteroaryl groups are optionally substituted with up to three non-hydrogen substituents independently selected from $C_{1-6}$ alkyl, substituted $C_{1-6}$ alkyl, halo, and $C_{2-6}$ alkynyl substituted with phenyl.

In one embodiment n is 0. In another embodiment n is 1. In a further embodiment Cy is 2-furanyl. In yet another embodiment Cy is 2-furanyl substituted with halo. In one embodiment Cy is 2-furanyl substituted with chlorine. In yet a further embodiment n is O and Cy is 2-furanyl optionally substituted with halo. In one embodiment n is 1 and Cy is 2-furanyl optionally substituted with halo. In yet another embodiment 2-furanyl is substituted on position 5. In another embodiment R' and R" are independently selected from methyl, ethyl, n-propyl, isopropyl, n-butyl, i-butyl, s-butyl or t-butyl. In a further embodiment R' and R" are independently selected from phenyl or benzyl.

In some cases, compounds of the present invention are chiral. The present invention includes all enantiomeric or diastereomeric forms of such compounds.

Representative compounds of the present invention include the following:

N-(furan-2-ylcarbonyl)-3,7-diazabicyclo[3.3.0]octane,
N-(3-methylfuran-2-ylcarbonyl)-3,7-diazabicyclo[3.3.0]octane,
N-(5-methylfuran-2-ylcarbonyl)-3,7-diazabicyclo[3.3.0]octane,
N-(3-chlorofuran-2-ylcarbonyl)-3,7-diazabicyclo[3.3.0]octane,
N-(5-chlorofuran-2-ylcarbonyl)-3,7-diazabicyclo[3.3.0]octane,
N-(3-bromofuran-2-ylcarbonyl)-3,7-diazabicyclo[3.3.0]octane,
N-(5-bromofuran-2-ylcarbonyl)-3,7-diazabicyclo[3.3.0]octane,
N-(4-phenylfuran-2-ylcarbonyl)-3,7-diazabicyclo[3.3.0]octane,
N-(5-(2-pyridinyl)furan-2-ylcarbonyl)-3,7-diazabicyclo[3.3.0]octane,
N-(5-(phenylethynyl)furan-2-ylcarbonyl)-3,7-diazabicyclo[3.3.0]octane,
N-(furan-3-ylcarbonyl)-3,7-diazabicyclo[3.3.0]octane,
N-(oxazol-2-ylcarbonyl)-3,7-diazabicyclo[3.3.0]octane,
N-(oxazol-4-ylcarbonyl)-3,7-diazabicyclo[3.3.0]octane,
N-(oxazol-5-ylcarbonyl)-3,7-diazabicyclo[3.3.0]octane,
N-(isoxazol-3-ylcarbonyl)-3,7-diazabicyclo[3.3.0]octane,
N-(isoxazol-4-ylcarbonyl)-3,7-diazabicyclo[3.3.0]octane,
N-(isoxazol-5-ylcarbonyl)-3,7-diazabicyclo[3.3.0]octane, N-(3-bromoisoxazol-5-ylcarbonyl)-3,7-diazabicyclo[3.3.0]octane,
N-(3-methoxyisoxazol-5-ylcarbonyl)-3,7-diazabicyclo[3.3.0]octane,
N-(1,2,4-oxadiazol-3-ylcarbonyl)-3,7-diazabicyclo[3.3.0]octane,
N-(1,2,4-oxadiazol-5-ylcarbonyl)-3,7-diazabicyclo[3.3.0]octane,
N-(1,3,4-oxadiazol-2-ylcarbonyl)-3,7-diazabicyclo[3.3.0]octane,
N-(thiazol-2-ylcarbonyl)-3,7-diazabicyclo[3.3.0]octane,
N-(thiazol-4-ylcarbonyl)-3,7-diazabicyclo[3.3.0]octane,
N-(thiazol-5-ylcarbonyl)-3,7-diazabicyclo[3.3.0]octane,
N-(isothiazol-3-ylcarbonyl)-3,7-diazabicyclo[3.3.0]octane,
N-(isothiazol-4-ylcarbonyl)-3,7-diazabicyclo[3.3.0]octane,
N-(isothiazol-5-ylcarbonyl)-3,7-diazabicyclo[3.3.0]octane,
N-(1,2,4-thiadiazol-3-ylcarbonyl)-3,7-diazabicyclo[3.3.0]octane,
N-(1,2,4-thiadiazol-5-ylcarbonyl)-3,7-diazabicyclo[3.3.0]octane,
N-(1,3,4-thiadiazol-2-ylcarbonyl)-3,7-diazabicyclo[3.3.0]octane,
N-(pyridin-4-ylcarbonyl)-3,7-diazabicyclo[3.3.0]octane,
and pharmaceutically acceptable salts thereof.

Representative compounds of the present invention also include the following:
N-(furan-2-ylcarbonyl)-3,7-diazabicyclo[3.3.1]nonane,
N-(3-methylfuran-2-ylcarbonyl)-3,7-diazabicyclo[3.3.1]nonane,
N-(5-methylfuran-2-ylcarbonyl)-3,7-diazabicyclo[3.3.1]nonane,
N-(3-chlorofuran-2-ylcarbonyl)-3,7-diazabicyclo[3.3.1]nonane,
N-(5-chlorofuran-2-ylcarbonyl)-3,7-diazabicyclo[3.3.1]nonane,
N-(3-bromofuran-2-ylcarbonyl)-3,7-diazabicyclo[3.3.1]nonane,
N-(5-bromofuran-2-ylcarbonyl)-3,7-diazabicyclo[3.3.1]nonane,
N-(4-phenylfuran-2-ylcarbonyl)-3,7-diazabicyclo[3.3.1]nonane,
N-(5-(2-pyridinyl)furan-2-ylcarbonyl)-3,7-diazabicyclo[3.3.1]nonane,
N-(5-(phenylethynyl)furan-2-ylcarbonyl)-3,7-diazabicyclo[3.3.1]nonane,
N-(furan-3-ylcarbonyl)-3,7-diazabicyclo[3.3.1]nonane,
N-(oxazol-2-ylcarbonyl)-3,7-diazabicyclo[3.3.1]nonane,
N-(oxazol-4-ylcarbonyl)-3,7-diazabicyclo[3.3.1]nonane,
N-(oxazol-5-ylcarbonyl)-3,7-diazabicyclo[3.3.1]nonane,
N-(isoxazol-3-ylcarbonyl)-3,7-diazabicyclo[3.3.1]nonane,
N-(isoxazol-4-ylcarbonyl)-3,7-diazabicyclo[3.3.1]nonane,
N-(isoxazol-5-ylcarbonyl)-3,7-diazabicyclo[3.3.1]nonane,
N-(3-bromoisoxazol-5-ylcarbonyl)-3,7-diazabicyclo[3.3.1]nonane,
N-(3-methoxyisoxazol-5-ylcarbonyl)-3,7-diazabicyclo[3.3.1]nonane,
N-(1,2,4-oxadiazol-3-ylcarbonyl)-3,7-diazabicyclo[3.3.1]nonane,
N-(1,2,4-oxadiazol-5-ylcarbonyl)-3,7-diazabicyclo[3.3.1]nonane,
N-(1,3,4-oxadiazol-2-ylcarbonyl)-3,7-diazabicyclo[3.3.1]nonane,
N-(thiazol-2-ylcarbonyl)-3,7-diazabicyclo[3.3.1]nonane,
N-(thiazol-4-ylcarbonyl)-3,7-diazabicyclo[3.3.1]nonane,
N-(thiazol-5-ylcarbonyl)-3,7-diazabicyclo[3.3.1]nonane,
N-(isothiazol-3-ylcarbonyl)-3,7-diazabicyclo[3.3.1]nonane,
N-(isothiazol-4-ylcarbonyl)-3,7-diazabicyclo[3.3.1]nonane,
N-(isothiazol-5-ylcarbonyl)-3,7-diazabicyclo[3.3.1]nonane,
N-(1,2,4-thiadiazol-3-ylcarbonyl)-3,7-diazabicyclo[3.3.1]nonane,
N-(1,2,4-thiadiazol-5-ylcarbonyl)-3,7-diazabicyclo[3.3.1]nonane,
N-(1,3,4-thiadiazol-2-ylcarbonyl)-3,7-diazabicyclo[3.3.1]nonane,
N-(pyridin-4-ylcarbonyl)-3,7-diazabicyclo[3.3.1]nonane,
and pharmaceutically acceptable salts thereof.

One embodiment relates to compound N-(5-chlorofuran-2-ylcarbonyl)-3,7-diazabicyclo[3.3.0]octane, or pharmaceutically acceptable salts thereof. Another embodiment relates to compound N-(5-chlorofuran-2-ylcarbonyl)-3,7-diazabicyclo[3.3.1]nonane, or pharmaceutically acceptable salts thereof.

Compound Preparation

The compounds of the present invention can be prepared via the coupling of mono-protected diazabicycle (i.e., one in which one of the two amine functional groups is rendered un-reactive by suitable derivatization) with a suitably functionalized heteroaryl acid chloride or other reactive carboxylic acid derivative.

There are numerous methods for preparing the mono-protected diazabicycles used to prepare the compounds of the present invention. Methods for the synthesis of a suitably protected 3,7-diazabicyclo[3.3.0]octane are described in PCT WO 02/070523 to Colon-Cruz et al. and in U.S. application 2006/0019985 to Zhenkun et al., in which N-benzylmaleimide is condensed with either paraformaldehyde and N-benzylglycine or N-(methoxymethyl)-N-(trimethylsilylmethyl)benzylamine to produce 3,7-dibenzyl-3,7-diazabicyclo[3.3.0]octane-2,4-dione (also known as 2,5-dibenzyltetrahydropyrrolo[3,4-c]pyrrole-1,3-dione). Subsequent transformation of this intermediate can follow several paths. In one instance, treatment with α-chloroethylchloroformate produces 3-benzyl-3,7-diazabicyclo[3.3.0]octane-2,4-dione (also known as 2-benzyltetrahydropyrrolo[3,4-c]pyrrole-1,3-dione), which is then sequentially reduced (using borane-dimethylsulfide complex), converted into its N-(tert-butoxycarbonyl) derivative, and hydrogenated (to remove the second benzyl group). This produces N-(tert-butoxycarbonyl)-3,7-diazabicyclo[3.3.0]octane, which can be used in coupling with carboxylic acids, and their derivatives, to produce compounds of the present invention. Alternately, 3,7-dibenzyl-3,7-diazabicyclo[3.3.0]octane-2,4-dione can be reduced (with lithium aluminum hydride), partially hydrogenated (to remove one benzyl group), converted into its N-(tert-butoxycarbonyl) derivative, and hydrogenated (to remove the second benzyl group), to produce N-(tert-butoxycarbonyl)-3,7-diazabicyclo[3.3.0]octane. Other methods for installation and removal of the benzyl, tert-butoxycarbonyl, and other amine protecting groups are well known by those skilled in the art and are described further in T. W. Greene and P. G. M. Wuts, Protective Groups in Organic Synthesis, 3$^{rd}$ Edition, John Wiley & Sons, New York (1999).

An alternative preparation of N-(tert-butoxycarbonyl)-3,7-diazabicyclo[3.3.0]octane has been described in U.S. applications 2004/0186107 to Schrimpf et al. and 2005/0101602 to Basha et al., and involves the condensation of maleimide and N-(methoxymethyl)-N-(trimethylsilylmethyl)benzylamine to give 7-benzyl-3,7-diazabicyclo[3.3.0]octane-2,4-dione (also known as 5-benzyltetrahydropyrrolo[3,4-c]pyrrole-1,3-dione). Subsequent treatment with a reducing agent (e.g., lithium aluminum hydride) produces the 3-benzyl-3,7-diazabicyclo[3.3.0]octane, the free amine of which can be protected by a tert-butoxycabonyl group, followed by removal of the benzyl protecting group by hydrogenolysis.

Maleate esters can be used as alternatives to maleimides in these condensation reactions. Thus, according to PCT WO 96/007656 to Schaus et al., condensation of N-benzylglycine with paraformaldehyde and dimethylmaleate will give N-benzyl-cis-3,4-pyrrolidinedicarboxylic acid dimethyl ester. This compound can then be reduced, for example, with lithium aluminum hydride, to give the diol, which can be further reacted with methanesulfonyl chloride in the presence of triethylamine to produce the corresponding dimesylate. Further treatment with ammonia and heat provides the N-benzyl protected 3,7-diazabicyclo[3.3.0]octane. As described above, this can be converted into N-(tert-butoxycarbonyl)-3,7-diazabicyclo[3.3.0]octane.

Suitable derivatives of 3,7-diazabicyclo[3.3.1]nonane (bispidine) can be used to make compounds of the present invention. One such derivative is N-(tert-butoxycarbonyl)-3,7-diazabicyclo[3.3.1]nonane, which can be made in a variety of ways. One synthesis proceeds through N-benzyl-N'-(tert-butoxycarbonyl)-3,7-diazabicyclo[3.3.1]nonane, described by Stead et al. in *Org. Leu.* 7: 4459 (2005). Thus the Mannich reaction between N-(tert-butoxycarbonyl)piperidin-4-one, benzylamine and paraformaldehyde affords N-benzyl-N'-(tert-butoxycarbonyl)-3,7-diazabicyclo[3.3.1]nonan-9-one, which can be treated sequentially with p-toluenesulfonhydrazide and sodium borohydride (to remove the carbonyl oxygen), giving N-benzyl-N'-(tert-butoxycarbonyl)-3,7-diazabicyclo[3.3.1]nonane. The benzyl group can be removed as described above to provide N-(tert-butoxycarbonyl)-3,7-diazabicyclo[3.3.1]nonane. Alternative syntheses of diazabicyclo[3.3.1]nonanes, suitable for conversion to either N-(tert-butoxycarbonyl)-3,7-diazabicyclo[3.3.1]nonane or another mono-protected derivative, have been described by Jeyaraman and Avila in *Chem. Rev.* 81(2): 149-174 (1981) and in U.S. Pat. No. 5,468,858 to Berlin et al.

One means of making amides of the present invention is to couple the either N-(tert-butoxycarbonyl)-3,7-diazabicyclo [3.3.0]octane or N-(tert-butoxycarbonyl)-3,7-diazabicyclo [3.3.1]nonane with a suitably functionalized carboxylic acid and then remove the tert-butoxycarbonyl protecting group. Many such carboxylic acids are commercially available, and others can be easily prepared by procedures known to those skilled in the art. The condensation of an amine and a carboxylic acid, to produce an amide, typically requires the use of a suitable activating agent, such as N,N'-dicyclohexylcarbodiimide (DCC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), O-(benzotriazol-1-yl)-N,N, N',N'-bis(tetramethylene)uronium hexafluorophosphate (HBPyU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), or (1-ethyl-3-(3-dimethylaminopropyl)carbodiimide) (EDCI) with 1-hydroxybenzotriazole (HOBt). Other activating agents are well known to those skilled in the art (for example, see Kiso and Yajima, Peptides, pp 39-91, Academic Press, San Diego, Calif. (1995)).

Alternatively, the amide bond can be formed by coupling a mono-protected diazabicycle with a suitably functionalized acid chloride, which may be available commercially or may be prepared by conversion of the suitably functionalized carboxylic acid. The acid chloride may be prepared by treatment of the appropriate carboxylic acid with, among other reagents, thionyl chloride or oxalyl chloride.

After amide formation, removal of the protecting group (e.g., the tert-butoxycarbonyl group) with acid, either aqueous or anhydrous, will afford the compounds of the present invention.

Those skilled in the art of organic synthesis will appreciate that there exist multiple means of producing compounds of the present invention which are labeled with a radioisotope appropriate to various diagnostic uses. Thus, condensation of a $^{11}$C- or $^{18}$F-labeled heteroaromatic carboxylic acid with either N-(tert-butoxycarbonyl)-3,7-diazabicyclo[3.3.0]octane or N-(tert-butoxycarbonyl)-3,7-diazabicyclo[3.3.1] nonane, using the methods described above, and subsequent removal of the tert-butoxycarbonyl group will produce a compound suitable for use in positron emission tomography.

Methods of Treatment

The compounds of the present invention are modulators of the α4β2 NNR subtype, characteristic of the CNS, and can be used for preventing and/or treating various conditions or disorders, including those of the CNS, in subjects which have or are susceptible to such conditions or disorders, by modulation of α4β2 NNRs. The compounds have the ability to selectively bind to the α4β2 NNRs and express nicotinic pharmacology (e.g., to act as agonists, partial agonists, antagonists and the like). For example, compounds of the present invention, when administered in effective amounts to patients in need thereof, provide some degree of prevention of the progression of the CNS disorder (i.e., providing protective effects), amelioration of the symptoms of the CNS disorder, and/or amelioration of the reoccurrence of the CNS disorder.

The compounds of the present invention can be used to treat and/or prevent those types of conditions and disorders for which other types of nicotinic compounds have been proposed as therapeutics. See, for example, the references previously listed in the "Background of the Invention" section, as well as Williams et al., *Drug News Perspec.* 7(4): 205 (1994), Arneric et al., *CNS Drug Rev.* 1(1): 1-26 (1995), Arneric et al., *Exp. Opin. Invest. Drugs* 5(1): 79-100 (1996), Bencherif et al., *J. Pharmacol. Exp. Ther.* 279: 1413 (1996), Lippiello et al., *J. Pharmacol. Exp. Ther.* 279: 1422 (1996), Damaj et al., *J. Pharmacol. Exp. Ther.* 291: 390 (1999); Chiari et al., *Anesthesiology* 91: 1447 (1999), Lavand'homme and Eisenbach, *Anesthesiology* 91: 1455 (1999), Holladay et al., *J. Med. Chem.* 40(28): 4169-94 (1997), Bannon et al., *Science* 279: 77 (1998), PCT WO 94/08992, PCT WO 96/31475, PCT WO 96/40682, and U.S. Pat. Nos. 5,583,140 to Bencherif et al., 5,597,919 to Dull et al., 5,604,231 to Smith et al. and 5,852,041 to Cosford et al., the disclosures of which are incorporated herein by reference in their entirety.

The compounds and their pharmaceutical compositions are useful in the treatment and/or prevention of a variety of CNS disorders, including neurodegenerative disorders, neuropsychiatric disorders, neurologic disorders, and addictions. The compounds and their pharmaceutical compositions can be used to treat and/or prevent cognitive deficits (age-related and otherwise), attentional disorders and dementias (including those due to infectious agents or metabolic disturbances); to provide neuroprotection; to treat convulsions and multiple cerebral infarcts; to treat mood disorders, compulsions and addictive behaviors; to provide analgesia; to control inflammation (such as mediated by cytokines and nuclear factor kappa B) and treat inflammatory disorders; to provide pain relief; and to treat infections (as anti-infectious agents for treating bacterial, fungal and viral infections). Among the disorders, diseases and conditions that the compounds and pharmaceutical compositions of the present invention can be used to treat and/or prevent are: age-associated memory impairment, mild cognitive impairment, pre-senile dementia (early onset Alzheimer's disease), senile dementia (dementia of the Alzheimer's type), Lewy body dementia, HIV-dementia, vascular dementia, Alzheimer's disease, stroke, AIDS dementia complex, attention deficit disorder, attention deficit hyperactivity disorder, dyslexia, schizophrenia, schizophreniform disorder, schizoaffective disorder, Parkinsonism including Parkinson's disease, Pick's disease, Huntington's chorea, tardive dyskinesia, hyperkinesia, progressive supranuclear palsy, Creutzfeld-Jakob disease, multiple sclerosis, amyotrophic lateral sclerosis, epilepsy, mania, anxiety, depression, panic disorders, bipolar disorders, generalized anxiety disorder, obsessive compulsive disorder, rage outbursts, Tourette's syndrome, autism, drug and alcohol addiction, tobacco addiction, obesity, cachexia, psoriasis, lupus, acute cholangitis, aphthous stomatitis, asthma, ulcerative colitis, inflammatory bowel disease, pouchitis, viral pneumonitis and arthritis (e.g., rheumatoid arthritis and osteoarthritis), endotoxaemia, sepsis, atherosclerosis, idiopathic pulmonary fibrosis and neoplasias.

It is advantageous that the treatment or prevention of diseases, disorders and conditions occurs without appreciable adverse side effects (e.g., significant increases in blood pressure and heart rate, significant negative effects upon the gastro-intestinal tract, and significant effects upon skeletal muscle). The compounds of the present invention, when employed in effective amounts, can modulate the activity of the $\alpha 4 \beta 2$ NNRs without appreciable interaction with the nicotinic subtypes that characterize the human ganglia (as demonstrated by their lack of the ability of to elicit nicotinic function in adrenal chromaffin tissue) or skeletal muscle (as demonstrated by their lack of ability to elicit nicotinic function in cell preparations expressing muscle-type nicotinic receptors). Thus, these compounds are capable of treating and/or preventing diseases, disorders and conditions without eliciting significant side effects associated activity at ganglionic and neuromuscular sites. Thus, administration of the compounds provides a therapeutic window in which treatment of certain diseases, disorders and conditions is provided, and certain side effects are avoided. That is, an effective dose of the compound is sufficient to provide the desired effects upon the disease, disorder or condition, but is insufficient (i.e., is not at a high enough level) to provide undesirable side effects.

Thus, the present invention provides the use of a compound or Formula I, or a pharmaceutically acceptable salt thereof, for use in therapy (such as a therapy described above).

In yet another aspect the present invention provides the use of a compound or Formula I, or a pharmaceutically acceptable salt thereof, in the manufacture of a medicament for use in the treatment of a CNS disorder (such as a disorder, disease or condition described above).

In a further aspect the invention provides the use of a compound of Formula I, or a pharmaceutically acceptable salt thereof, in the manufacture of a medicament for use in the treatment mild to moderate dementia of the Alzheimer's type, attention deficit disorder, mild cognitive impairment and age associated memory impairment.

Diagnostic Uses

The compounds can be used in diagnostic compositions, such as probes, particularly when they are modified to include appropriate labels. The probes can be used, for example, to determine the relative number and/or function of specific receptors, particularly the $\alpha 4 \beta 2$ receptor subtype. For this purpose the compounds of the present invention most preferably are labeled with a radioactive isotopic moiety such as $^{11}C$, $^{18}F$, $^{76}Br$, $^{123}I$ or $^{125}I$.

The administered compounds can be detected using known detection methods appropriate for the label used. Examples of detection methods include position emission topography (PET) and single-photon emission computed tomography (SPECT). The radiolabels described above are useful in PET (e.g., $^{11}C$, $^{18}F$ or $^{76}Br$) and SPECT (e.g., $^{23}I$) imaging, with half-lives of about 20.4 minutes for $^{11}C$, about 109 minutes for $^{18}F$, about 13 hours for $^{123}I$, and about 16 hours for $^{76}Br$. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al. The compounds can be administered in formulation compositions that incorporate other ingredients, such as those types of ingredients that are useful in formulating a diagnostic composition. Compounds useful in accordance with carrying out the present invention most preferably are employed in forms of high purity. See, U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected NNR subtypes. In addition to humans, the compounds can also be administered to animals, such as mice, rats, dogs, and monkeys. SPECT and PET imaging can be carried out using any appropriate technique and apparatus. See Villemagne et al., In: Arneric et al. (Eds.) *Neuronal Nicotinic Receptors: Pharmacology and Therapeutic Opportunities*, 235-250 (1998) and U.S. Pat. No. 5,853,696 to Elmalch et al. for a disclosure of representative imaging techniques.

The radiolabeled compounds bind with high affinity to selective NNR subtypes (e.g., $\alpha 4 \beta 2$) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected NNR subtypes (e.g., $\alpha 4 \beta 2$ receptor subtype). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes (e.g., the α4β2 receptor subtype).

Pharmaceutical Compositions

According to one embodiment of the present invention there is provided a pharmaceutical composition comprising as active ingredient a therapeutically effective amount of a compound of the present invention, in association with one or more pharmaceutically acceptable diluents, excipients and/or inert carriers.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intravenously, intramuscularly, subcutaneously, intraperitoneally, intraarterially, intrathecally, and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); transdermally (e.g., using a transdermal patch, using technology that is commercially available from Novartis and Alza Corporation, or by powder injection); or by buccal, sublingual or intranasal absorption. Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. For example, the compositions can be administered in the form of a tablet, a hard gelatin capsule or as a time release capsule. These formulations may contain a liquid carrier that may be oily, aqueous, emulsified or contain certain solvents suitable to the mode of administration.

The administration of the pharmaceutical compositions described herein can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical composition is administered can vary.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to modulate the activity of relevant nicotinic receptor subtypes (e.g., modulate neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate disease-relevant receptors to affect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular and ganglionic effects are observed.

Typically, to be administered in an effective dose, compounds require administering in an amount of less than 5 mg/kg of patient weight. Often, the compounds may be administered in an amount from less than about 1 mg/kg patient weight to less than about 100 ng/kg of patient weight, and occasionally between about 10 ng/kg to less than 100 ng/kg of patient weight. The foregoing effective doses typically represent that amount administered as a single dose, or as one or more doses administered over a 24 hours period. For human patients, the effective dose of the compounds may require administering the compound in an amount of at least about 1, but not more than about 1000, and often not more than about 500 mg/24 hr/patient.

Compositions useful as diagnostics can be employed, as set forth in U.S. Pat. Nos. 5,853,696 to Elmalch et al. and 5,969,144 to London et al., the contents of which are hereby incorporated by reference. The compounds also can be administered in formulation compositions that incorporate other ingredients, such as those types of ingredients that are useful in formulating a diagnostic composition.

The following examples are provided to illustrate the present invention, and should not be construed as limiting thereof. In these examples, all parts and percentages are by weight, unless otherwise noted.

Biological Assays

EXAMPLE 1

Radioligand Binding at CNS nAChRs

α4β2 nAChR Subtype

Preparation of Membranes from Rat Cortex: Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, and then decapitated. Brains were removed and placed on an ice-cold platform. The cerebral cortex was removed and placed in 20 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C.

Preparation of Membranes from SH-EP1/Human α4β2 Clonal Cells: Cell pellets from 40 150 mm culture dishes were pooled, and homogenized by Polytron (Kinematica GmbH, Switzerland) in 20 milliliters of ice-cold preparative buffer. The homogenate was centrifuged at 48,000 g for 20 minutes at 4° C. The resulting pellet was re-suspended in 20 mL of ice-cold preparative buffer and stored at −20° C.

On the day of the assay, the frozen membranes were thawed and spun at 48,000×g for 20 min. The supernatant was decanted and discarded. The pellet was resuspended in Dulbecco's phosphate buffered saline (PBS, Life Technologies) pH 7.4 and homogenized with the Polytron for 6 seconds. Protein concentrations were determined using a Pierce BCA Protein Assay Kit, with bovine serum albumin as the standard (Pierce Chemical Company, Rockford, Ill.).

Membrane preparations (approximately 50 μg for human and 200-300 μg protein for rat α4β2) were incubated in PBS (50 μL and 100 μL respectively) in the presence of competitor compound (0.01 nM to 100 μM) and 5 nM [$^3$H]nicotine for 2-3 hours on ice. Incubation was terminated by rapid filtration on a multi-manifold tissue harvester (Brandel, Gaithersburg, Md.) using GF/B filters presoaked in 0.33% polyethyleneimine (w/v) to reduce non-specific binding. Tissue was rinsed 3 times in PBS, pH 7.4. Scintillation fluid was added to filters containing the washed tissue and allowed to equilibrate. Filters were then counted to determine radioactivity bound to the membranes by liquid scintillation counting (2200CA Tri-Carb LSC, Packard Instruments, 50% efficiency or Wallac Trilux 1450 MicroBeta, 40% efficiency, Perkin Elmer).

Data were expressed as disintegrations per minute (DPMs). Within each assay, each point had 2-3 replicates. The replicates for each point were averaged and plotted against the log of the drug concentration. $IC_{50}$, which is the concentration of the compound that produces 50% inhibition of binding, was determined by least squares non-linear regression. Ki values were calculated using the Cheng-Prussof equation (1973):

$Ki=IC_{50}/(1+N/Kd)$ where N is the concentration of [$^3$H]nicotine and Kd is the affinity of nicotine (3 nM, determined in a separate experiment).

α7 nAChR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The hippocampus was removed and placed in 10 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 2 mg protein/mL. Protein was determined by the method of Lowry et al., *J. Biol. Chem.* 193: 265 (1951), using bovine serum albumin as the standard.

The binding of [$^3$H]MLA was measured using a modification of the methods of Davies et al., *Neuropharmacol.* 38: 679 (1999). [$^3$H]MLA (Specific Activity=25-35 Ci/mmol) was obtained from Tocris. The binding of [$^3$H]MLA was determined using a 2 h incubation at 21° C. Incubations were conducted in 48-well micro-titre plates and contained about 200 μg of protein per well in a final incubation volume of 300 μL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters were soaked in de-ionized water containing 0.33% polyethyleneimine to reduce non-specific binding. Each filter was washed with PBS (3×1 mL) at room temperature. Non-specific binding was determined by inclusion of 50 μM non-radioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., *Biochem. Pharmacol.* 22: 3099-3108 (1973).

EXAMPLE 2

Determination of Dopamine Release

Dopamine release was measured using striatal synaptosomes obtained from rat brain, according to the procedures set forth by Rapier et al., *J. Neurochem.* 54: 937 (1990). Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. The brains were quickly removed and the striata dissected. Striatal tissue from each of 2 rats was pooled and homogenized in ice-cold 0.32 M sucrose (5 mL) containing 5 mM HEPES, pH 7.4, using a glass/glass homogenizer. The tissue was then centrifuged at 1,000×g for 10 min. The pellet was discarded and the supernatant was centrifuged at 12,000×g for 20 min. The resulting pellet was re-suspended in perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline HCl and 10 mM glucose, pH 7.4) and centrifuged for 15 min at 25,000×g. The final pellet was resuspended in perfusion buffer (1.4 mL) for immediate use.

The synaptosomal suspension was incubated for 10 min at 37° C. to restore metabolic activity. [$^3$H]Dopamine ([$^3$H]DA, specific activity=28.0 Ci/mmol, NEN Research Products) was added at a final concentration of 0.1 μM and the suspension was incubated at 37° C. for another 10 min. Aliquots of tissue (50 μL) and perfusion buffer (100 μL) were loaded into the suprafusion chambers of a Brandel Suprafusion System (series 2500, Gaithersburg, Md.). Perfusion buffer (room temperature) was pumped into the chambers at a rate of 1.5 mL/min for a wash period of 16 min. Test compound (10 μM) or nicotine (10 μM) was then applied in the perfusion stream for 48 sec. Fractions (24 sec each) were continuously collected from each chamber throughout the experiment to capture basal release and agonist-induced peak release and to re-establish the baseline after the agonist application. The perfusate was collected directly into scintillation vials, to which scintillation fluid was added. [$^3$H]DA released was quantified by scintillation counting. For each chamber, the integrated area of the peak was normalized to its baseline.

Release was expressed as a percentage of release obtained with an equal concentration of L-nicotine. Within each assay, each test compound was replicated using 2-3 chambers; replicates were averaged. When appropriate, dose-response curves of test compound were determined The maximal activation for individual compounds (Emax) was determined as a percentage of the maximal activation induced by L-nicotine. The compound concentration resulting in half maximal activation ($EC_{50}$) of specific ion flux was also defined.

EXAMPLE 3

Selectivity vs. Peripheral nAChRs

Interaction at the Human Muscle nAChR Subtype

Activation of muscle-type nAChRs was established on the human clonal line TE671/RD, which is derived from an embryonal rhabdomyosarcoma (Stratton et al., Carcinogen 10: 899 (1989)). These cells express receptors that have pharmacological (Lukas, *J. Pharmacol. Exp. Ther.* 251: 175 (1989)), electrophysiological (Oswald et al., *Neurosci. Lett.* 96: 207 (1989)), and molecular biological profiles (Luther et al., *J. Neurosci.* 9: 1082 (1989)) similar to the muscle-type nAChR.

TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 12 well polystyrene plates (Costar). Experiments were conducted when the cells reached 100% confluency.

Nicotinic acetylcholine receptor (nAChR) function was assayed using $^{86}Rb^+$ efflux according to the method described by Lukas et al., *Anal. Biochem.* 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 nM of test compound, 100 μM of L-nicotine (Acros Organics) or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 nM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Rat Ganglionic nAChR Subtype

Activation of rat ganglion nAChRs was established on the pheochromocytoma clonal line PC12, which is a continuous clonal cell line of neural crest origin, derived from a tumor of the rat adrenal medulla. These cells express ganglion-like nAChR s (see Whiting et al., *Nature* 327: 515 (1987); Lukas, *J. Pharmacol. Exp. Ther.* 251: 175 (1989); Whiting et al., *Mol. Brain. Res.* 10: 61 (1990)).

Rat PC12 cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 12 well Nunc plates (Nunclon) and coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 μM of test compound, 100 μM of nicotine or buffer alone for 4 min. Following the exposure period, the supernatant containing the released $^{86}Rb^+$ was removed and transferred to scintillation vials. Scintillation fluid was added and released radioactivity was measured by liquid scintillation counting Within each assay, each point had 2 replicates, which were averaged. The amount of $^{86}Rb^+$ release was compared to both a positive control (100 nM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Human Ganglionic nAChR Subtype

The cell line SH-SY5Y is a continuous line derived by sequential subcloning of the parental cell line, SK-N-SH, which was originally obtained from a human peripheral neuroblastoma. SH-SY5Y cells express a ganglion-like nAChR (Lukas et al., *Mol. Cell. Neurosci.* 4: 1 (1993)).

Human SH-SY5Y cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (Hy-Clone, Logan Utah), 1 mM sodium pyruvate, 4 mM L-Glutamine, and 50,000 units penicillin-streptomycin (Irvine Scientific). When cells were 80% confluent, they were plated to 12 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4), taking care not to disturb the cells. Next, cells were exposed to either 100 μM of test compound, 100 μM of nicotine, or buffer alone for 4 min. Following the exposure period, the supernatant containing the released $^{86}Rb^+$ was removed and transferred to scintillation vials. Scintillation fluid was added and released radioactivity was measured by liquid scintillation counting Within each assay, each point had 2 replicates, which were averaged. The amount of $^{86}Rb^+$ release was compared to both a positive control (100 μM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

EXAMPLE 4

Novel Object Recognition (NOR) Task

The novel object recognition (NOR) task was performed in accord with the description of Ennaceur and Delacour *Behav. Brain Res.* 100: 85-92 (1988).

SYNTHETIC EXAMPLES

EXAMPLE 5

Synthesis of N-(tert-butoxycarbonyl)-3,7-diazabicyclo[3.3.0]octane

Example 5 relates to the synthesis of N-(tert-butoxycarbonyl)-3,7-diazabicyclo[3.3.0]octane, which was prepared as described in U.S. applications 2004/0186107 to Schrimpf et al. and 2005/0101602 to Basha et al., according to the following techniques:

5-Benzyltetrahydropyrrolo[3,4-c]pyrrole-1,3-dione
(or 7-benzyl-3,7-diazabicyclo[3.3.0]octan-2,4-dione)

Trifluoroacetic acid (TFA, 0.50 mL, 6.5 mmol) was added to a cold (0° C.) solution of maleimide (6.27 g, 0.0646 mol) in dichloromethane (150 mL) under nitrogen. A solution of N-(methoxymethyl)-N-(trimethylsilylmethyl)benzylamine (20 g, 0.084 mol) in dichloromethane (100 mL) was added drop-wise over 45 min. After the addition was complete, the mixture was warmed slowly to ambient temperature and stirred for 16 h. The mixture was concentrated and the resulting residue was dissolved in dichloromethane (200 mL) and washed with saturated aqueous sodium bicarbonate (2×50 mL). The aqueous layer was separated and extracted with dichloromethane (2×75 mL). The combined dichloromethane extracts were washed with brine (50 mL), dried over anhydrous magnesium sulfate, filtered and concentrated to give 12.5 g (83.9% yield) of a light yellow, waxy solid (MS m/z 231 (M+H)).

2-Benzyloctahydropyrrolo[3,4-c]pyrrole (or
3-benzyl-3,7-diazabicyclo[3.3.0]octane)

The crude 5-benzyltetrahydropyrrolo[3,4-c]pyrrole-1,3-dione (4.9 g, 0.021 mol) was dissolved in cold (0° C.) dry tetrahydrofuran (THF) (50 mL) under nitrogen, and lithium aluminum hydride (63 mL of 1 M in THF, 0.063 mol) was added drop-wise over 30 min to the continuously cooled solution. The resulting mixture was stirred at ambient temperature for 30 min and then warmed to reflux for 4 h. The mixture was then cooled to 0° C. and quenched by the slow addition of excess solid sodium sulfate decahydrate. The mixture was warmed to ambient temperature and stirred for 16 h. The solids were filtered and the residue was washed with ethyl acetate (3×100 mL). The combined filtrates were concentrated to give 4.2 g (99% yield) of a waxy solid (MS m/z 203 (M+H)).

5-Benzylhexahydropyrrolo[3,4-c]pyrrole-2-carboxylic acid tert-butyl ester (or N-benzyl-N'-(tert-butoxycarbonyl)-3,7-diazabicyclo[3.3.0]octane)

The crude 2-benzyloctahydropyrrolo[3,4-c]pyrrole (4.2 g, 0.021 mol) was dissolved in THF (50 mL). Di-t-butyl dicarbonate (5.5 g, 0.025 mol) and aqueous saturated $NaHCO_3$ (10 mL) were added, and the mixture was stirred at ambient temperature overnight. The reaction was quenched with water (10 mL), and ethyl acetate (30 mL) was added. The aqueous layer was extracted with ethyl acetate (2×20 mL), and the combined organic extracts were dried over anhydrous sodium sulfate and concentrated. Purification via silica gel column chromatography (1:1 hexanes/ethyl acetate) gave 5.07 g (79.8% yield) of the title compound (MS m/z 303 (M+H)).

Hexahydropyrrolo[3,4-c]pyrrole-2-carboxylic acid tert-butyl ester (or N-(tert-butoxycarbonyl)-3,7-diazabicyclo[3.3.0]octane)

The 5-benzylhexahydropyrrolo[3,4-c]pyrrole-2-carboxylic acid tert-butyl ester (5.07 g, 0.0168 mol) was dissolved in methanol (50 mL) and 20% Pd(OH)$_2$/C (wet) (~2 g) was added under a nitrogen atmosphere. The resulting mixture was warmed (45-50° C.) and shaken for 2 h under 40 psi of hydrogen. The mixture was filtered and concentrated to give 3.49 g (97.7% yield) of the title compound (MS m/z 213 (M+H)).

EXAMPLE 6

Synthesis of N-(furan-2-ylcarbonyl)-3,7-diazabicyclo[3.3.0]octane

Example 6 relates to the synthesis of furan-2-yl(hexahydropyrrolo[3,4-c]pyrrol-2-yl)methanone (or N-(furan-2-ylcarbonyl)-3,7-diazabicyclo[3.3.0]octane), which was prepared according to the following techniques, illustrative of the coupling reaction used to make heteroaromatic amides of 3,7-diazabicyclo[3.3.0]octane:

Furan-2-yl(hexahydropyrrolo[3,4-c]pyrrol-2-yl) methanone trifluoroacetate (or N-(furan-2-ylcarbonyl)-3,7-diazabicyclo[3.3.0]octane trifluoroacetate)

Furan-2-carboxylic acid (0.037 g, 0.33 mmol) and triethylamine (0.125 mL, 0.99 mmol) were combined in dry dichloromethane (1 mL), and O-(benzotriazol-1-yl)-1,1,3,3,-tetramethyluronium hexafluorophosphate (HBTU; 0.125 g, 0.33 mmol) was added. A solution of hexahydropyrrolo[3,4-c]pyrrole-2-carboxylic acid tert-butyl ester (0.064 g, 0.30 mmol) in dichloromethane (0.5 mL) was added, and the mixture was stirred at ambient temperature overnight. The mixture was shaken with 10% aqueous sodium hydroxide, and the organic layer was separated. The aqueous layer was extracted with chloroform (2×2 mL). The combined organic extracts were washed with water (2×1 mL) and concentrated. The resulting residue was dissolved in dimethylformamide (DMF) (0.3 mL) and purified by HPLC (acetonitrile/water gradient). Fractions containing the desired material were pooled and concentrated, leaving the tert-butoxycarbonyl-protected product. This material was dissolved in a mixture of trifluoroacetic acid (0.5 mL) and dichloromethane (0.5 mL), and the mixture was stirred at ambient temperature for 1 h. The volatiles were removed by rotary evaporation, followed by high vacuum treatment, to give 77 mg of an oil (80% yield) ($^1$H NMR (d$_4$-methanol, 300 MHz) 3.20 (m, 2H), 3.47-4.2 (m, 8H), 6.60 (t, 1H), 7.18 (d, 1H), 7.72 (d, 1H); MS m/z 207 (M+H)).

EXAMPLE 7

Synthesis of N-(5-chlorofuran-2-ylcarbonyl)-3,7-diazabicyclo[3.3.0]octane trifluoroacetate Example 7 relates to the synthesis of 5-chlorofuran-2-yl (hexahydropyrrolo[3,4-c]pyrrol-2-yl)methanone trifluoroacetate (or N-(5-chlorofuran-2-ylcarbonyl)-3,7-diazabicyclo[3.3.0]octane trofluoroacetate), which was prepared according to the following techniques, illustrative of the coupling reaction used to make heteroaromatic amides of 3,7-diazabicyclo[3.3.0]octane:

5-Chlorofuran-2-carboxylic acid

Aqueous sodium hydroxide (80 mL of 10%) was added to a solution of silver nitrate (8.0 g, 47 mmol) in water (20 mL). This suspension was stirred and slowly treated with 30% aqueous ammonium hydroxide until it became clear. A solution of 5-chlorofuran-2-carboxaldehyde (3.0 g, 23 mmol) (Aldrich Chemical) in methanol (5 mL) was added, and the resulting mixture was stirred at ambient temperature for 30 min. The reaction mixture was filtered, and the filtrate was washed with ether (100 mL). The aqueous filtrate was then made acidic (~pH 3) by the addition of cold 20% sulfuric acid. The resulting mixture was extracted with ethyl acetate (3×100 mL). The extracts were washed with saturated aqueous sodium chloride solution (100 mL), dried (anhydrous sodium sulfate) and concentrated under vacuum to give 3.2 g (95% yield) of white solid (mp 178-179° C.). This reaction was easily scalable and was run multiple times at >10 g scale.

N-(5-chlorofuran-2-ylcarbonyl)-3,7-diazabicyclo [3.3.0]octane trifluoroacetate

Oxalyl chloride (12.2 g, 95.8 mmol) containing a drop of DMF was added drop-wise to an ice-cooled solution of 5-chlorofuran-2-carboxylic acid (6.25 g, 47.9 mmol) in 200 mL of dichloromethane. After complete addition, the ice bath was removed and the reaction was warmed to ambient temperature over a 1 h period. The volatiles were then removed under vacuum, and the residue was dissolved in THF (50 mL). This solution of the acid chloride was then added to an stirred, ice-cooled solution of hexahydropyrrolo[3,4-c]pyrrole-2-carboxylic acid tert-butyl ester (10.2 g, 47.9 mmol) and diisopropylethylamine (25 g, ~4 equivalents) in THF (200 mL). This mixture was stirred at ambient temperature for 16 h. The volatiles were then removed under vacuum, and the residue was partitioned between water (100 mL) and ether (300 mL). The ether layer and two ether extracts (100 mL) of the aqueous layer were concentrated on the rotary evaporator. The residue was column chromatographed on silica gel, eluting with a 0-60% ethyl acetate in hexane gradient. Concentration of selected fractions gave 13.9 g (85.3% yield) of pale yellow syrup. A portion of this material (12.9 g, 37.9 mmol) was dissolved in a mixture of dichloromethane and trifluoroacetic acid (100 mL each). This mixture was stirred at ambient temperature for 2 h and then concentrated under vacuum. The residue was partitioned between chloroform (200 mL) and 50% aqueous potassium carbonate (200 mL), and the aqueous layer was extracted with chloroform (3×200 mL). The combined chloroform layers were dried over anhydrous sodium sulfate and concentrated under vacuum, leaving 8.66 g (95% yield) of pale yellow solid ($^1$H NMR (d$_4$-methanol, 300 MHz) 3.15-3.35 (m, 4H), 3.50-4.20 (m, 6H), 6.51 (d, 1H), 7.17 (d, 1H); MS m/z 241 (M+H)).

EXAMPLE 8

Synthesis of 3,7-diazabicyclo[3.3.1]nonane-3-carboxylic acid tert-butyl ester

Example 8 relates to the synthesis of 3,7-diazabicyclo [3.3.1]nonane-3-carboxylic acid tert-butyl ester (or N-(tert-butoxycarbonyl)-3,7-diazabicyclo[3.3.1]nonane), which was prepared according to the following techniques:

7-Benzyl-3,7-diazabicyclo[3.3.1]nonane-3-carboxylic acid tert-butyl ester (or N-benzyl-N'-(tert-butoxycarbonyl)-3,7-diazabicyclo[3.3.1]nonane)

7-Benzyl-3,7-diazabicyclo[3.3.1]nonane-3-carboxylic acid tert-butyl ester was prepared according to procedures set forth by Stead et al. in *Org. Leu.* 7(20): 4459 (2005).

3,7-Diazabicyclo[3.3.1]-3-carboxylic acid tert-butyl ester

7-Benzyl-3,7-diazabicyclo[3.3.1]nonane-3-carboxylic acid tert-butyl ester (0.49 g, 1.6 mmol) was dissolved in methanol (20 mL) and 20% Pd(OH)$_2$/C (wet) (~2 g) was added under a nitrogen atmosphere. This mixture was warmed to about 50° C. and shaken for 2 h under 55 psi of hydrogen. The resulting mixture was filtered and concentrated to give 0.32 g (94% yield) of the title compound (MS m/z 227 (M+H)).

EXAMPLE 9

Synthesis of N-(furan-2-ylcarbonyl)-3,7-diazabicyclo[3.3.1]nonane trifluoroacetate Example 9 relates to the synthesis of (3,7-diazabicyclo[3.3.1]non-3-yl)-furan-2-ylmethanone trifluoroacetate (or N-(furan-2-ylcarbonyl)-3,7-diazabicyclo[3.3.1]nonane trifluoroacetate), which was prepared according to the following techniques, illustrative of the coupling reaction used to make heteroaromatic amides of 3,7-diazabicyclo[3.3.1]nonane:

3,7-Diazabicyclo[3.3.1]non-3-yl)-furan-2-yl methanone trifluoroacetate (or N-(furan-2-ylcarbonyl)-3,7-diazabicyclo[3.3.1]nonane trifluoroacetate)

Furan-2-carboxylic acid (0.032 g, 0.29 mmol) was combined with triethylamine (0.870 mmol, 0.121 mL) in dry dichloromethane (1 mL) and HBTU (0.11 g, 0.29 mmol) was added. A solution of 3,7-diazabicyclo[3.3.1]-3-carboxylic acid tert-butyl ester (0.059 g, 0.26 mmol) in dichloromethane (0.5 mL) was added, and the mixture was stirred at ambient temperature overnight. The mixture was treated with 10% aqueous sodium hydroxide and extracted with chloroform (2×2 mL). The combined organic extracts were washed with water (2×1 mL), and concentrated. The resulting residue was dissolved in DMF (0.3 mL) and purified by HPLC (acetonitrile/water gradient). Fractions containing the desired material were pooled and concentrated, leaving the tert-butoxycarbonyl-protected product. This material was dissolved in a mixture of trifluoroacetic acid (0.5 mL) and dichloromethane (0.5 mL), and the mixture was stirred at ambient temperature for 1 h. The volatiles were removed by rotary evaporation, followed by high vacuum treatment, to give 36 mg of an oil (41% yield) ($^1$H NMR (d$_4$-methanol, 300 MHz) 2.10 (bs, 2H), 2.35 (bs, 2H), 3.30-3.45 (m, 4H), 3.55 (m, 2H), 6.65 (m, 1H), 7.15 (d, 1H), and 7.75 (d, 1H). MS m/z 221 (M+H)).

EXAMPLE 10

Synthesis of N-(5-chlorofuran-2-ylcarbonyl)-3,7-diazabicyclo[3.3.1]nonane trifluoroacetate Example 10 relates to the synthesis of (3,7-diazabicyclo[3.3.1]non-3-yl)-5-chlorofuran-2-ylmethanone trifluoroacetate (or N-(5-chlorofuran-2-ylcarbonyl)-3,7-diazabicyclo[3.3.1]nonane trifluoroacetate), which was prepared by a process similar to that described in Example 9, according to the following techniques:

5-Chlorofuran-2-carboxylic acid (0.96 g, 6.5 mmol) was combined with triethylamine (21 mmol, 2.9 mL) in dry dichloromethane (10 mL), and HBTU (2.47 g, 65.1 mmol) was added. A solution of 3,7-diazabicyclo[3.3.1]-3-carboxylic acid tert-butyl ester (1.5 g, 66 mmol) in dichloromethane (5 mL) was added, and the mixture was stirred at ambient temperature overnight. The mixture was treated with 10% aqueous sodium hydroxide and extracted with chloroform (2×20 mL). The combined organic extracts were washed with water (2×10 mL), and concentrated. The resulting residue was purified by column chromatography on silica gel, eluting with an ethyl acetate in hexane gradient, to give the tert-butoxycarbonyl-protected product, as a viscous oil. This material was dissolved in a mixture of trifluoroacetic acid (20 mL) and dichloromethane (20 mL), and the mixture was stirred at ambient temperature for 1 h. The volatiles were removed by rotary evaporation, followed by high vacuum treatment, to give 1.38 g (57.5% yield) of viscous yellow oil ($^1$H NMR (d$_4$-methanol, 300 MHz) 2.00 (bs, 2H), 2.15 (bs, 2H), 3.15-3.35 (m, 6H), 4.25 (m, 2H), 6.53 (d, 1H) and 7.10 (d, 1H). MS m/z 255 (M+H)).

EXAMPLE 11

Tabular Spectral and Receptor Binding Data

The above illustrated amide coupling procedures were utilized to make the compounds shown in Tables 1 and 2. In some cases, compounds were synthesized on a scale sufficient to obtain nuclear magnetic resonance (NMR) data. In other cases, compounds were produced on a smaller scale in various kinds of parallel synthesis apparatus and were (structurally) characterized by LCMS only.

TABLE 1

| Structure | Rat α4β2 Ki | Human α4β2 Ki | α7 Ki | MS: m/z (M + H) | $^1$H NMR: CD$_3$OD, 300 MHz |
|---|---|---|---|---|---|
| 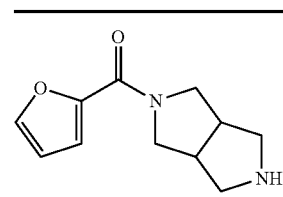 | 20 | 33 | 13000 | 207 | δ 7.72 (d, 1H), 7.18 (d, 1H), 6.60 (t, 1H), 3.47-4.2 (m, 8H), 3.2 (m, 2H) |

TABLE 1-continued
| Structure | Rat α4β2 Ki | Human α4β2 Ki | α7 Ki | MS: m/z (M + H) | ¹H NMR: CD₃OD, 300 MHz |
|---|---|---|---|---|---|
| 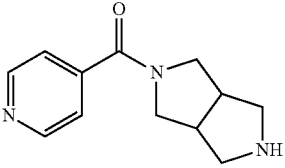 [SMILES: O=C(c1ccncc1)N1CC2CNCC2C1] | 26 | 160 | ND; failed HTS | 218 | δ 9.00 (d, 2H), 8.20 (m, 2H), 3.7-4.0 (m, 3H), 3.47-3.7 (m, 5H), 3.2 (m, 2H) |
| 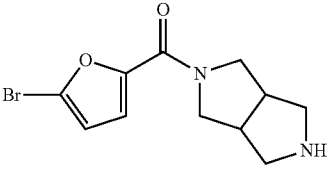 [SMILES: O=C(c1ccc(Br)o1)N1CC2CNCC2C1] | 54 | 73 | 12000 | 287 | |
| 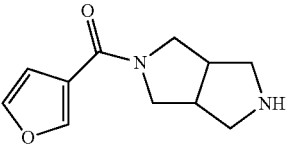 [SMILES: O=C(c1ccoc1)N1CC2CNCC2C1] | 53 | 220 | 3100 | 207 | |
| 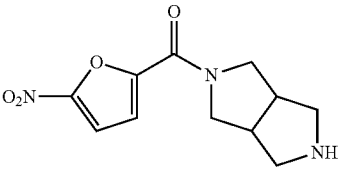 [SMILES: O=C(c1ccc([N+](=O)[O-])o1)N1CC2CNCC2C1] | 35 | 31 | 2900 | 252 | |
| 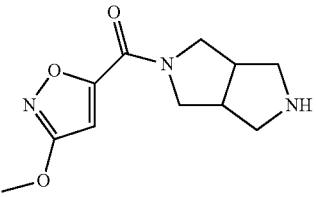 [SMILES: COc1cc(C(=O)N2CC3CNCC3C2)on1] | 19 | 19 | 3500 | 238 | |
| 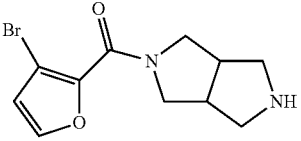 [SMILES: O=C(c1occc1Br)N1CC2CNCC2C1] | 1.5 | 1.5 | 12000 | 287 | |
| 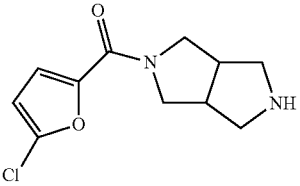 [SMILES: O=C(c1ccc(Cl)o1)N1CC2CNCC2C1] | 33 | 28 | 91000 | 241 | δ 7.17 (d, J = 0.61 Hz, 1H), 6.51 (d, J = 0.73 Hz, 1H), 4.20-3.50 (m, 6H), 3.35-3.15 (m, 4H) |
| 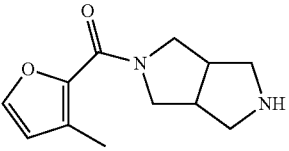 [SMILES: Cc1ccoc1C(=O)N1CC2CNCC2C1] | 44 | 54 | 25000 | 221 | |

TABLE 1-continued
| Structure | Rat α4β2 Ki | Human α4β2 Ki | α7 Ki | MS: m/z (M + H) | ¹H NMR: CD₃OD, 300 MHz |
|---|---|---|---|---|---|
| 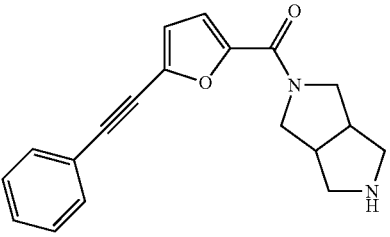 [SMILES: O=C(c1ccc(C#Cc2ccccc2)o1)N1CC2CNCC2C1] | 230 | 43 | 3200 | 307 | |
| 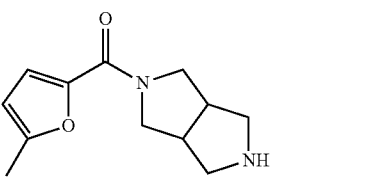 [SMILES: Cc1ccc(C(=O)N2CC3CNCC3C2)o1] | 130 | 28 | 23000 | 221 | |
| 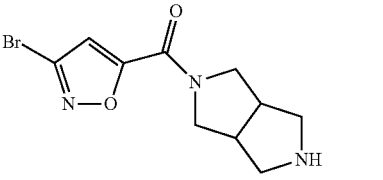 [SMILES: O=C(c1cc(Br)no1)N1CC2CNCC2C1] | 17 | 44 | ND; failed HTS | 288 | |
| 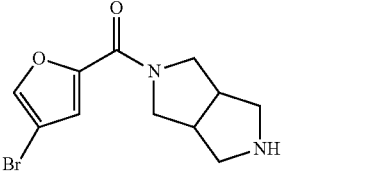 [SMILES: O=C(c1cc(Br)co1)N1CC2CNCC2C1] | 29 | 18 | ND; failed HTS | 287 | δ 7.80 (s, 1H), 7.2 (s, 1H), 3.5-4.2 (m, 8H), 3.20 (m, 2H) |
| 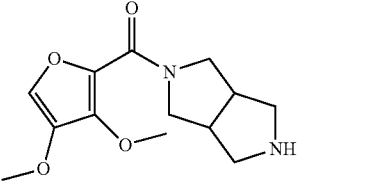 [SMILES: COc1coc(C(=O)N2CC3CNCC3C2)c1OC] | 140 | 40 | ND; failed HTS | 267 | |
| 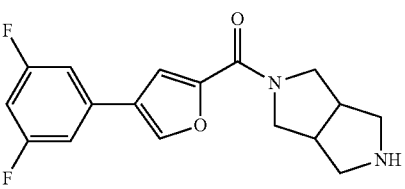 [SMILES: O=C(c1cc(-c2cc(F)cc(F)c2)co1)N1CC2CNCC2C1] | 54 | 24 | ND; failed HTS | 319 | δ 7.50 (s, 1H), 7.17 (m, 2H), 6.78 (m, 1H), 6.60 (s, 1H), 3.95-3.76 (m, 4H), 3.70-3.58 (m, 2H), 3.32-3.08 (m, 4H) |
| 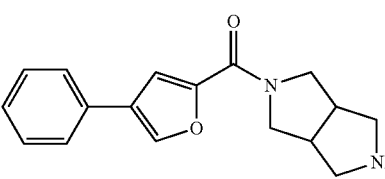 | 260 | 86 | 12000 | 283 | |
| 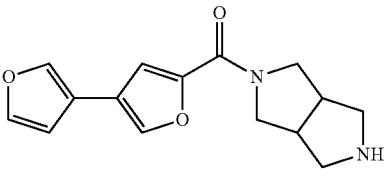 [SMILES: O=C(c1cc(-c2ccoc2)co1)N1CC2CNCC2C1] | 110 | 95 | ND; failed HTS | 273 | |

TABLE 1-continued

| Structure | Rat α4β2 Ki | Human α4β2 Ki | α7 Ki | MS: m/z (M + H) | ¹H NMR: CD₃OD, 300 MHz |
|---|---|---|---|---|---|
| (5-methylisoxazol-3-yl)-octahydropyrrolo[3,4-b]pyrrole carbonyl | 150 | 84 | ND; failed HTS | 222 | |
| (4-methyloxazol-5-yl)-octahydropyrrolo[3,4-b]pyrrole carbonyl | 15 | 9.2 | 210000 | 222 | |
| (3-methylisoxazol-4-yl)-octahydropyrrolo[3,4-b]pyrrole carbonyl | 24 | 14 | 56000 | 222 | |
| (3-methylisoxazol-5-yl)-octahydropyrrolo[3,4-b]pyrrole carbonyl | 32 | 31 | ND; failed HTS | 222 | |
| (2-methylfuran-3-yl)-octahydropyrrolo[3,4-b]pyrrole carbonyl | 61 | 29 | 160000 | 221 | δ 7.38 (d, J = 1.8 Hz, 1 H), 6.55 (d, J = 1.8 Hz, 1 H), 3.79 (m, 2 H), 3.45 (m, 2 H), 3.06 (m, 2 H), 2.89 (m, 2 H), 2.67 (m, 2 H), 2.37 (s, 3H) |
| (5-carbamoylfuran-2-yl)-octahydropyrrolo[3,4-b]pyrrole carbonyl | 53 | 63 | ND; failed HTS | 250 | |
| (3-methoxyfuran-2-yl)-octahydropyrrolo[3,4-b]pyrrole carbonyl | 353 | 100 | ND; failed HTS | 237 | δ 7.55 (s, 1H), 6.7-6.6 (m, 1H), 3.9 (s, 3H), 3.85 (m, 2H), 3.75 (m, 2H), 3.65 (m, 2H), 3.15 (m, 4H) |
| (3-trifluoromethyl-5-methylfuran-2-yl)-octahydropyrrolo[3,4-b]pyrrole carbonyl | 1000 | 45 | ND; failed HTS | 289 | δ 6.48 (s, 1H), 3.5-4.0 (m, 6H), 3.3-3.1 (m, 4H), 2.35 (s, 3H) |

TABLE 1-continued

| Structure | Rat α4β2 Ki | Human α4β2 Ki | α7 Ki | MS: m/z (M + H) | ¹H NMR: CD₃OD, 300 MHz |
|---|---|---|---|---|---|
| CF₃-furan-C(O)-octahydropyrrolo[3,4-c]pyrrole | 320 | 36 | ND; failed HTS | 275 | δ 8.25 (s, 1H), 7.35 (s, 1H), 4.2-3.6 (m, 4H), 3.55 (dd, 2H), 3.3-3.2 (m, 4H) |
| NH₂SO₂-furan-C(O)-octahydropyrrolo[3,4-c]pyrrole | 31 | 28 | ND; failed HTS | 286 | δ 8.15 (s, 1H), 7.35 (s, 1H), 4.2-3.6 (m, 4H), 3.5 (dd, 2H), 3.4-3.2 (m, 4H) |
| Br, methyl-furan-C(O)-octahydropyrrolo[3,4-c]pyrrole | 20 | 22 | ND; failed HTS | 299/301 | |
| vinyl-furan-C(O)-octahydropyrrolo[3,4-c]pyrrole | 140 | 51 | ND; failed HTS | 233 | δ 7.58 (dd, J = 2, 0.5 Hz, 1H), 7.26 (dd, J = 18, 11 Hz, 1H), 6.86 (dd, J = 2, 0.5 Hz, 1H), 5.70 (dd, J = 18, 1.5 Hz, 1H), 5.32 (dd, J = 11, 1.5 Hz, 1H), 4.20-3.62 (m, 4H), 3.62-3.58 (m, 2H), 3.25-3.18 (m, 4H) |
| pentynyl-furan-C(O)-octahydropyrrolo[3,4-c]pyrrole | 43 | 21 | ND; failed HTS | 287 | δ 7.81 (s, 1H), 7.08 (d, J = 1 Hz, 1H), 4.18-3.62 (m, 4H), 3.59 (m, 2H), 3.30-3.20 (m, 4H), 2.40 (t, J = 7 Hz, 2H), 1.60-1.44 (m, 4H), 0.95 (t, J = 7 Hz, 3H) |
| Cl-furan-C(O)-octahydropyrrolo[3,4-c]pyrrole | 2.8 | 2.4 | ND; failed HTS | 241 | |
| F-furan-C(O)-octahydropyrrolo[3,4-c]pyrrole | 8.3 | 16 | ND; failed HTS | 225 | |
| Br,Br-furan-C(O)-octahydropyrrolo[3,4-c]pyrrole | 20 | 4.9 | ND; failed HTS | 366 | |

TABLE 1-continued

| Structure | Rat α4β2 Ki | Human α4β2 Ki | α7 Ki | MS: m/z (M + H) | 1H NMR: CD3OD, 300 MHz |
|---|---|---|---|---|---|
| (3-fluorofuran-2-carbonyl octahydropyrrolo[3,4-c]pyrrole) | 35 | 27 | ND; failed HTS | 225 | δ 7.60 (d, J = 2 Hz, 1H), 7.59 (d, J = 2 Hz, 1H), 4.18-3.65 (m, 4H), 3.60 (m, 2H), 3.22 (m, 4H) |
| (3-cyanofuran-2-carbonyl octahydropyrrolo[3,4-c]pyrrole) | 25 | 14 | ND; failed HTS | 232 | δ 7.85 (d, J = 2 Hz, 1H), 6.95 (d, J = 2 Hz, 1H), 4.25-3.63 (m, 4H), 3.60 (m, 2H), 3.24 (m, 4H) |
| (4-chlorofuran-2-carbonyl octahydropyrrolo[3,4-c]pyrrole) | 21 | 9.7 | ND; failed HTS | 241 | δ 7.83 (d, J = 1 Hz, 1H), 7.16 (d, J = 0.7 Hz, 1H), 4.20-3.62 (m, 4H), 3.60 (m, 2H), 3.28-3.19 (m, 4H) |
| (isoxazole-3-carbonyl octahydropyrrolo[3,4-c]pyrrole) | 89 | 90 | ND; failed HTS | 208 | δ 8.79 (d, J = 1.7 Hz, 1H), 6.80 (d, J = 1.7 Hz, 1H), 4.12 (dd, J = 12, 7 Hz, 1H), 3.99 (dd, J = 12, 3 Hz, 1H), 3.90 (dd, J = 13, 8 Hz, 1H), 3.75 (dd, J = 13, 4 Hz, 1H), 3.58 (m, 2H), 3.24 (m, 4H) |
| (4-fluorofuran-2-carbonyl octahydropyrrolo[3,4-c]pyrrole) | 36 | 21 | ND; failed HTS | 225 | δ 7.80 (d, J = 1 Hz, 1H), 7.78 (d, J = 1 Hz, 1H), 4.21-3.62 (m, 4H), 3.58 (m, 2H), 3.21 (m, 4H) |
| (5-ethynylfuran-2-carbonyl octahydropyrrolo[3,4-c]pyrrole) | 140 | 48 | ND; failed HTS | 231 | |
| (5-cyanofuran-2-carbonyl octahydropyrrolo[3,4-c]pyrrole) | 50 | 40 | ND; failed HTS | 232 | |
| (3-fluoro-5-methylfuran-2-carbonyl octahydropyrrolo[3,4-c]pyrrole) | 65 | 14 | ND; failed HTS | 239 | δ 6.24 (s, 1H), 4.17-3.65 (m, 4H), 3.57 (m, 2H), 3.19 (m, 4H), 2.34 (s, 3H) |

TABLE 1-continued
| Structure | Rat α4β2 Ki | Human α4β2 Ki | α7 Ki | MS: m/z (M + H) | ¹H NMR: CD₃OD, 300 MHz |
|---|---|---|---|---|---|
| 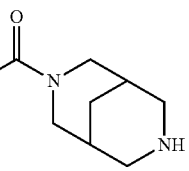 | 51 | 130 | ND; failed HTS | 257 | |
| 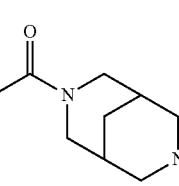 | 43 | 69 | ND; failed HTS | 208.3 | δ 8.52 (d, J = 2 Hz, 1H), 6.96 (d, J = 2 Hz, 1H), 4.15 (dd, J = 8, 12 Hz, 1H), 3.91 (m, 2H), 3.72 (dd, J = 4, 14 Hz, 1H), 3.60 (m, 2H), 3.33-3.23 (m, 4H). |
TABLE 2
| Structure | Rat α4β2 Ki | Human α4β2 Ki | α7 Ki | MS: m/z (M + H) | ¹H NMR: CD₃OD, 300 MHz |
|---|---|---|---|---|---|
| 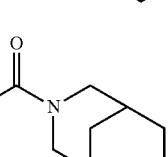 | 31 | 9.9 | 15000 | 221 | δ 7.75 (d, 1H), 7.15 (d, 1H), 6.65 (m, 1H), 4.55 (m, 2H), 3.55 (m, 2H), 3.3-3.45 (m, 4H), 2.35 (bs, 2H), 2.1 (bs, 2H) |
| 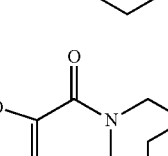 | 110 | 18 | 1700 | 232 | |
| 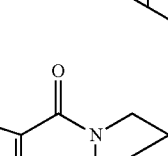 | 79 | 17 | ND; failed HTS | 301 | |
| 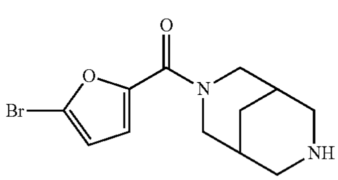 | 41 | 51 | ND; failed HTS | 301 | |
| 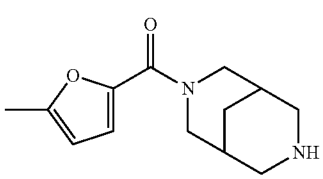 [SMILES: Cc1ccc(C(=O)N2CC3CNCC(C3)C2)o1] | 100 | 42 | ND; failed HTS | 235 | |

TABLE 2-continued
| Structure | Rat α4β2 Ki | Human α4β2 Ki | α7 Ki | MS: m/z (M + H) | ¹H NMR: CD₃OD, 300 MHz |
|---|---|---|---|---|---|
| 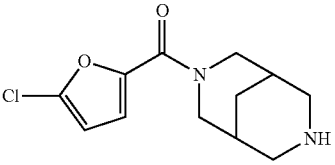 | 15 | 7.3 | 120000 | 255 | δ 7.10 (d, 1H), 6.53 (d, 1H), 4.25 (m, 2H), 3.15-3.35 (m, 6H), 2.15 (bs, 2H), 2.0 (bs, 2H) |
| 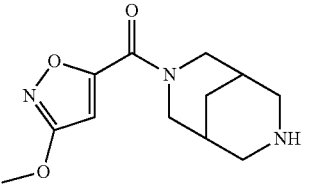 [SMILES: COc1cc(C(=O)N2CC3CNCC(C3)C2)on1] | 33 | 180 | ND; failed HTS | 252 | |
| 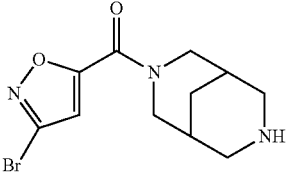 [SMILES: O=C(c1cc(Br)no1)N1CC2CNCC(C2)C1] | 5.9 | 18 | ND; failed HTS | 302 | |
| 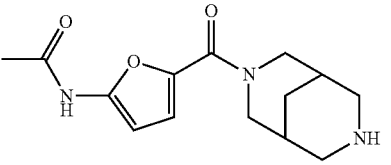 [SMILES: CC(=O)Nc1ccc(C(=O)N2CC3CNCC(C3)C2)o1] | 87 | 210 | ND; failed HTS | 278 | δ 7.18 (d, 1H), 6.36 (d, 1H), 4.56 (m, 2H), 3.58 (m, 2H), 3.40-3.24 (m, 4H), 2.30 (m, 2H), 2.18 (s, 3H), 2.05 (m, 2H) |
| 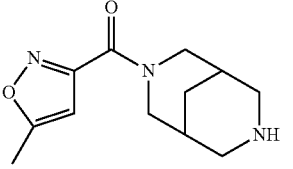 [SMILES: Cc1cc(C(=O)N2CC3CNCC(C3)C2)no1] | 68 | 96 | ND; failed HTS | 236 | |
| 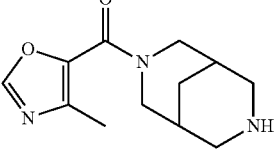 | 20 | 64 | ND; failed HTS | 236 | |
| 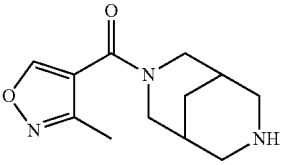 [SMILES: Cc1nocc1C(=O)N1CC2CNCC(C2)C1] | 9.5 | 21 | ND; failed HTS | 236 | |
| 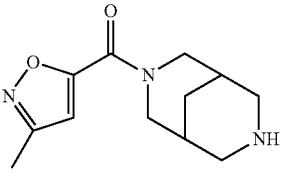 [SMILES: Cc1cc(C(=O)N2CC3CNCC(C3)C2)on1] | 29 | 47 | ND; failed HTS | 236 | |

TABLE 2-continued
| Structure | Rat α4β2 Ki | Human α4β2 Ki | α7 Ki | MS: m/z (M + H) | ¹H NMR: CD₃OD, 300 MHz |
|---|---|---|---|---|---|
| 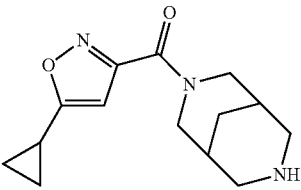 [SMILES: O=C(c1cc(C2CC2)on1)N1CC2CNCC(C2)C1] | 25 | 83 | ND; failed HTS | 262 | |
| 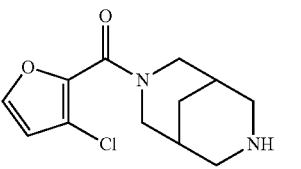 | 96 | 29 | ND; failed HTS | 255 | |
| 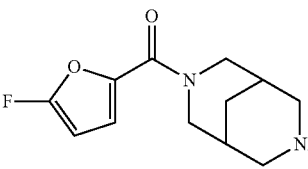 | 6.4 | 4.6 | ND; failed HTS | 239 | |
| 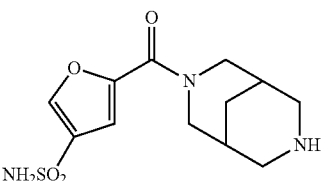 | 86 | 62 | ND; failed HTS | 300 | δ 8.19 (s, 1H), 7.3 (s, 1H), 4.45 (d, 2H), 3.6-3.2 (m, 6H), 2.27 (bs, 2H), 2.1-2.0 (m, 2H) |
| 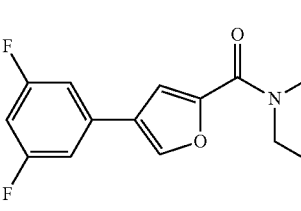 | 6.3 | 23 | ND; failed HTS | 333 | δ 8.22 (d, J = 1 Hz, 1H), 7.50 (d, J = 1 Hz, 1H), 7.27 (m, 2H), 6.90 (m, 1H), 4.55 (d, J = 13 Hz, 2H), 3.58 (m, 2H), 3.42-3.30 (m, 4H), 2.31 (bs, 2H), 2.06 (m, 2H) |
| 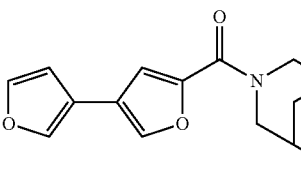 | 12 | 35 | ND; failed HTS | 287 | |
| 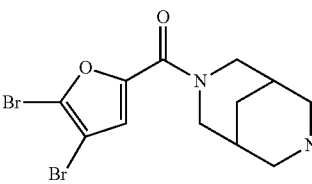 | 4 | 1.6 | ND; failed HTS | 380 | |
| 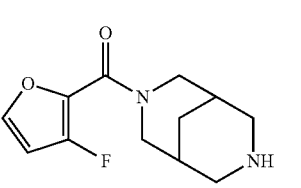 [SMILES: O=C(c1occc1F)N1CC2CNCC(C2)C1] | 110 | 57 | ND; failed HTS | 239 | δ 7.63 (dd, J = 4, 2 Hz, 1H), 6.62 (dd, J = 2, 1 Hz, 1H), 4.37 (d, J = 14 Hz, 2H), 3.50 (m, 2H), 3.34 (m, 4H), 2.28 (bs, 2H), 2.06 (m, 2H) |

TABLE 2-continued

| Structure | Rat α4β2 Ki | Human α4β2 Ki | α7 Ki | MS: m/z (M + H) | ¹H NMR: CD₃OD, 300 MHz |
|---|---|---|---|---|---|
| (furan with CN substituent, carbonyl linked to diazabicyclononane) | 110 | 31 | ND; failed HTS | 246 | |
| (4-chlorofuran-2-carbonyl diazabicyclononane) | 13 | 5.2 | ND; failed HTS | 255 | |
| (isoxazole-3-carbonyl diazabicyclononane) | 77 | 10 | ND; failed HTS | 255 | |
| (4-bromo-5-methylfuran-2-carbonyl diazabicyclononane) | 7.5 | 5.2 | ND; failed HTS | 313/315 | (CDCl₃) δ 6.95 (s, 1H), 4.60 (d, 2H), 3.55 (d, 2H), 3.38 (m, 2H), 3.25 (d, 2H), 2.35 (s, 3H), 2.25 (m, 2H), 2.05 (m, 2H) |
| (3-methoxyfuran-2-carbonyl diazabicyclononane) | 560 | 28 | ND; failed HTS | 251 | |
| (oxazole-5-carbonyl diazabicyclononane) | 28 | 26 | ND; failed HTS | 222 | |
| (4-fluorofuran-2-carbonyl diazabicyclononane) | 28 | 14 | ND; failed HTS | 239 | |
| (5-ethynylfuran-2-carbonyl diazabicyclononane) | 220 | 47 | ND; failed HTS | 245 | |

TABLE 2-continued

| Structure | Rat α4β2 Ki | Human α4β2 Ki | α7 Ki | MS: m/z (M + H) | ¹H NMR: CD₃OD, 300 MHz |
|---|---|---|---|---|---|
| (5-cyanofuran-2-yl structure) | 35 | 8.7 | ND; failed HTS | 246 | |
| (5-methyl-3-fluorofuran-2-yl structure) | 500 | 62 | ND; failed HTS | 253/505 | |
| (oxazol-2-yl structure) | 370 | 85 | ND; failed HTS | 222 | δ 8.09 (d, 1H), 7.40 (d, 1H), 3.65-3.23 (m, 8H), 2.30 (m, 2H), 2.05 (m, 2H) |
| (4-cyanofuran-2-yl structure) | 27 | 23 | ND; failed HTS | 246 | |
| (4-bromofuran-2-yl structure) | 12 | 1.7 | ND; failed HTS | 301 | |
| (5-methylisoxazol-4-yl structure) | 65 | 31 | ND; failed HTS | 236 | |
| (isoxazol-5-yl structure) | 52 | 30 | ND; failed HTS | 222 | δ 8.53 (d, 1H), 6.90 (d, 1H), 4.60-4.20 (m, 2H), 3.58-3.25 (m, 6H), 2.30 (m, 2H), 2.05 (m, 2H) |

Summary of Biological Data

Compounds of Tables 1 and 2, representative of the present invention, exhibited inhibition constants (Ki values) at the rat and human α4β2 subtypes in the ranges of 1 nM to 1000 nM and 1 nM to 220 nM respectively, indicating high affinity for the α4β2 subtype. Ki values at the α7 subtype vary within the range of 1700 nM to 210,000 nM (in many cases the compounds did not bind sufficiently in high through-put screening at the α7 subtype to warrant Ki determination). These same compounds exhibited relatively little functional activity at either the human muscle (1-25% of the maximal response to nicotine) or human ganglion (1-20% of the maximal response to nicotine) subtypes.

Figure 2:
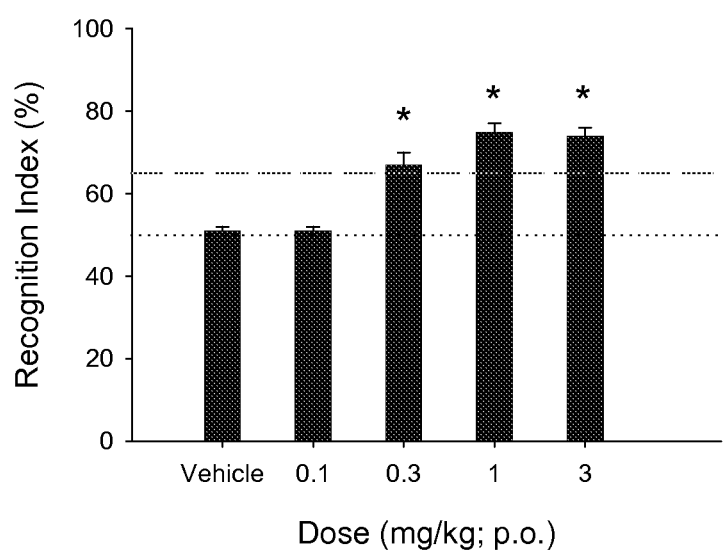
FIG. 2 is a chart showing the results of a study on object recognition in rats treated orally with N-(5-chlorofuran-2-ylcarbonyl)-3,7-diazabicyclo[3.3.1]nonane. The results are shown as a function of recognition index (%) versus dose (mg/kg).

Certain exemplified compounds were assessed in the NOR task. Thus, both N-(5-chlorofuran-2-ylcarbonyl)-3,7-diazabicyclo[3.3.0]octane (FIG. 1) and N-(5-chlorofuran-2-yl-carbonyl)-3,7-diazabicyclo[3.3.1]nonane (FIG. 2) were active in OR in rats, at 0.1 mg/kg and 0.3 mg/kg respectively. This provides evidence of the efficacy (and potency) of the compounds of the present invention in treating cognitive deficits, attentional disorders and dementias, and the potential of these compounds for human therapy.

The foregoing is illustrative of the present invention and is not to be construed as limiting thereof. The invention is defined by the following claims, with equivalents of the claims to be included therein. All patents and publications referred to herein are incorporated by reference in their entirety, for all purposes.

The invention claimed is:

1. A method for treating mild to moderate dementia of the Alzheimer's type, mild cognitive impairment, or age associated memory impairment comprising administering N-(5-chlorofuran-2-ylcarbonyl)-3,7-diazabicyclo[3.3.0]octane, or a pharmaceutically acceptable salt thereof, to a patient in need therof.

2. The method of claim 1, wherein the N-(5-chlorofuran-2-ylcarbonyl)-3,7-diazabicyclo[3.3.0]octane, or a pharmaceutically acceptable salt thereof is administered in a dose range of from about 100 µg/kg to about 1 mg/kg per day.

* * * * *